United States Patent
He et al.

(10) Patent No.: US 10,359,426 B2
(45) Date of Patent: *Jul. 23, 2019

(54) USE OF ISOCITRATE DEHYDROGENASE 1 AS A DIAGNOSTIC AND PROGNOSTIC BIOMARKER AND THERAPEUTIC TARGET FOR LUNG CANCERS

(71) Applicant: CANCER HOSPITAL, CHINESE ACADEMY OF MEDICAL SCIENCES, Beijing (CN)

(72) Inventors: Jie He, Beijing (CN); Fengwei Tan, Beijing (CN); Zhaoli Chen, Beijing (CN); Nan Sun, Beijing (CN)

(73) Assignee: Cancer Hospital, Chinese Academy of Medical Sciences, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/719,356

(22) Filed: Sep. 28, 2017

(65) Prior Publication Data
US 2018/0017563 A1 Jan. 18, 2018

Related U.S. Application Data

(62) Division of application No. 14/428,334, filed as application No. PCT/CN2012/081327 on Sep. 13, 2012, now Pat. No. 9,797,904.

(51) Int. Cl.
| | |
|---|---|
| *C12N 15/113* | (2010.01) |
| *G01N 33/574* | (2006.01) |
| *C07K 16/40* | (2006.01) |
| *C12Q 1/6886* | (2018.01) |

(52) U.S. Cl.
CPC ....... *G01N 33/57423* (2013.01); *C07K 16/40* (2013.01); *C12N 15/113* (2013.01); *C12Q 1/6886* (2013.01); *C12N 2310/14* (2013.01); *C12Q 2600/118* (2013.01); *C12Q 2600/158* (2013.01); *G01N 2333/904* (2013.01)

(58) Field of Classification Search
CPC .................................................... C12N 15/13
See application file for complete search history.

(56) References Cited

U.S. PATENT DOCUMENTS

| | | | |
|---|---|---|---|
| 9,797,904 B2 * | 10/2017 | He ...................... | C01Q 1/6886 |
| 2004/0067234 A1 | 4/2004 | Einat et al. | |

OTHER PUBLICATIONS

Hoffman, P. et al., "Lung cancer," Lancet, vol. 355, No. 9202, Feb. 5, 2000, 7 pages.
Chen, G. et al., "Proteomic Analysis of Lung Adenocarcinoma: Identification of a Highly Expressed Set of Proteins in Tumors," Clinical Cancer Research, vol. 8, No. 7, Jul. 2002, 9 pages.
Li, C. et al., "Proteomic Comparison of Two-Dimensional Gel Electrophoresis Profiles from Human Lung Squamous Carcinoma and Normal Bronchial Epithelial Tissues," Genomics, Proteomics & Bioinformatics, vol. 1, No. 1, Feb. 2003, 10 pages.
Li, C. et al., "Comparative proteomics analysis of human lung squamous carcinoma," Biochemical and Biophysical Research Communications, vol. 309, No. 1, Sep. 12, 2003, 8 pages.
Chen, G. et al., "Protein profiles associated with survival in lung adenocarcinoma," Proceedings of the National Academy of Sciences of the United States of America, vol. 100, No. 23, Nov. 11, 2003, Published Online Oct. 22, 2003, 6 pages.
Seike, M. et al., "Proteomic signature of human cancer cells," Proteomics, vol. 4, No. 9, Sep. 2004, Published Online Jul. 5, 2004, 13 pages.
Wu, X. et al., "Differential analysis of two-dimension gel electrophoresis profiles from the normal-metaplasia-dysplasia-carcinoma tissue of human bronchial epithelium," Pathology International, vol. 54, No. 10, Oct. 7, 2004, 9 pages.
Siolas, D. et al., "Synthetic shRNAs as potent RNAi triggers," Nature Biotechnology, vol. 23, No. 2, Feb. 2005, Published Online Dec. 26, 2004, 5 pages.
Maciel, C. et al., "Differential proteomic serum pattern of low molecular weight proteins expressed by adenocarcinoma lung cancer patients," Journal of Experimental Therapeutics & Oncology, vol. 5, No. 1, Available as Early as Mar. 2005, 9 pages.
Seike, M. et al., "Proteomic signatures for histological types of lung cancer," Proteomics, vol. 5, No. 11, Jul. 4, 2005, 10 pages.
Deng, B. et al., "Proteomics analysis of stage-specific proteins expressed in human squamous cell lung carcinoma tissues," Cancer Biomarkers, vol. 1, No. 6, Dec. 1, 2005, 8 pages.
Li, R. et al., "Identification of putative oncogenes in lung adenocarcinoma by a comprehensive functional genomic approach," Oncogene, vol. 25, No. 18, Apr. 27, 2006, Published Online Dec. 12, 2005, 8 pages.
Li, C. et al. "Proteome analysis of human lung squamous carcinoma," Proteomics, vol. 6, No. 2, Jan. 2006, 12 pages.
Huang, L. et al., "Proteomic Analysis of Secreted Proteins of Non-small Cell Lung Cancer," Chinese Journal of Cancer, vol. 25, No. 11, Nov. 2006, 9 pages.
Cho, W. et al., "Oncoproteomics: current trends and future perspectives," Expert Review of Proteomics, vol. 4, No. 3, Jun. 2007, 10 pages.
Simpson, R. et al., "Proteomics-driven cancer biomarker discovery: looking to the future," Current Opinion in Chemical Biology, vol. 12, No. 1, Feb. 2008, 6 pages.

(Continued)

Primary Examiner — J. E. Angell
(74) Attorney, Agent, or Firm — McCoy Russell LLP

(57) ABSTRACT

The present invention relates to a method for diagnosing lung cancers such as non-small lung cancer in a subject by using isocitrate dehydrogenase 1 as a diagnostic biomarker. The present invention also relates to a method for predicting the prognosis of the lung cancers such as non-small lung cancer in a subject by using isocitrate dehydrogenase 1 as a prognostic biomarker. The present invention further relates to a method of suppressing proliferation of lung tumor cells in a subject, decreasing growth of lung tumor cells in a subject, or improving survival of a subject with lung cancer by using isocitrate dehydrogenase 1 as a therapeutic target.

15 Claims, 12 Drawing Sheets
Specification includes a Sequence Listing.

(56) References Cited

OTHER PUBLICATIONS

Poschmann, G. et al., "Identification of Proteomic Differences between Squamous Cell Carcinoma of the Lung and Bronchial Epithelium," Molecular Cell & Proteomics, vol. 8, No. 5, May 2009, Published Online Jan. 27, 2009, 12 pages.
Dang, L. et al., "Cancer-associated IDH1 mutations produce 2-hydroxyglutarate," Nature, vol. 462, No. 7274, Dec. 10, 2009, Available Online Nov. 22, 2009, 8 pages.
Buhrens, R. et al., "Protein Expression in Human Non-Small Cell Lung Cancer: A Systematic Database," Pathobiology, vol. 76, No. 6, Dec. 2009, Published Online Nov. 30, 2009, 9 pages.
Jemal, A., et al., "Cancer Statistics, 2010," CA: A Cancer Journal for Clinicians, vol. 60, No. 5, Sep. 2010, Published Online Jul. 7, 2010, 24 pages.
Tan, F. et al., "Identification of Isocitrate Dehydrogenase 1 as a Potential Diagnostic and Prognostic Biomarker for Non-small Cell Lung Cancer by Proteomic Analysis," Molecular & Cellular Proteomics, vol. 11, No. 2, Feb. 2012, Published Online Nov. 7, 2011, 14 pages.
ISA State Intellectual Property Office of the People's Republic of China, International Search Report Issued in Application No. PCT/CN2012/081327, dated Jun. 20, 2013, WIPO, 4 pages.

\* cited by examiner

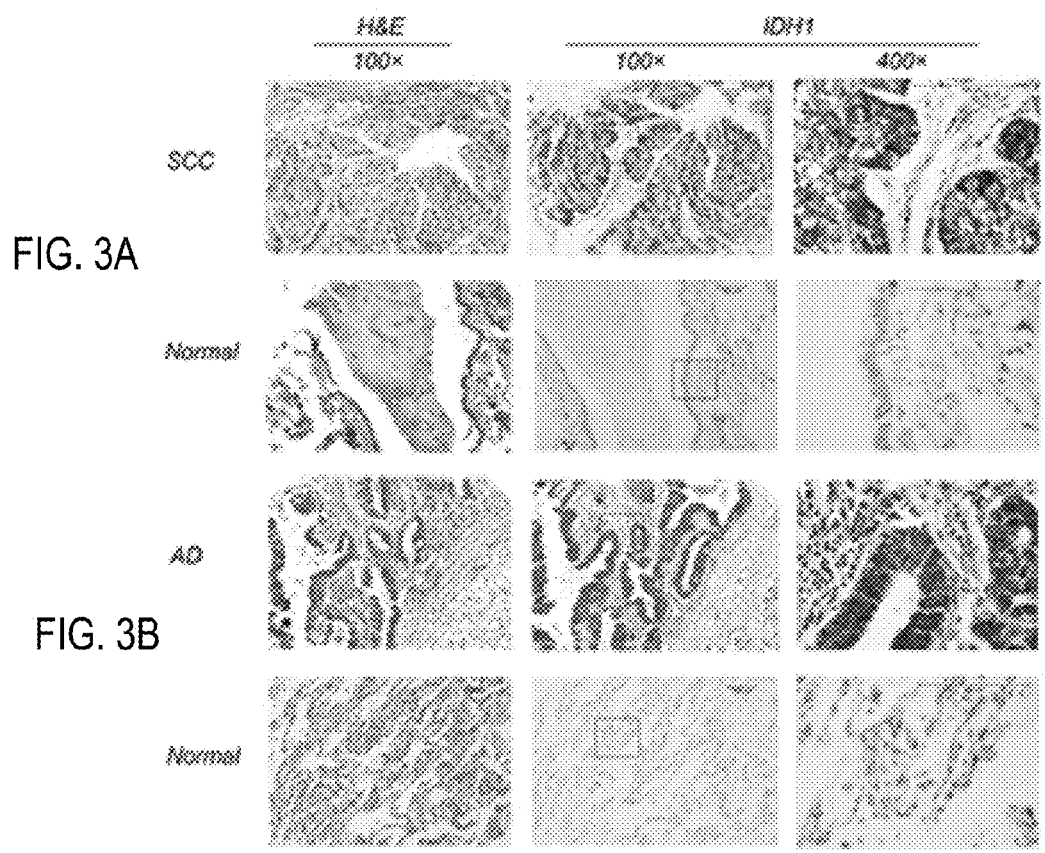
FIG. 3A
FIG. 3B
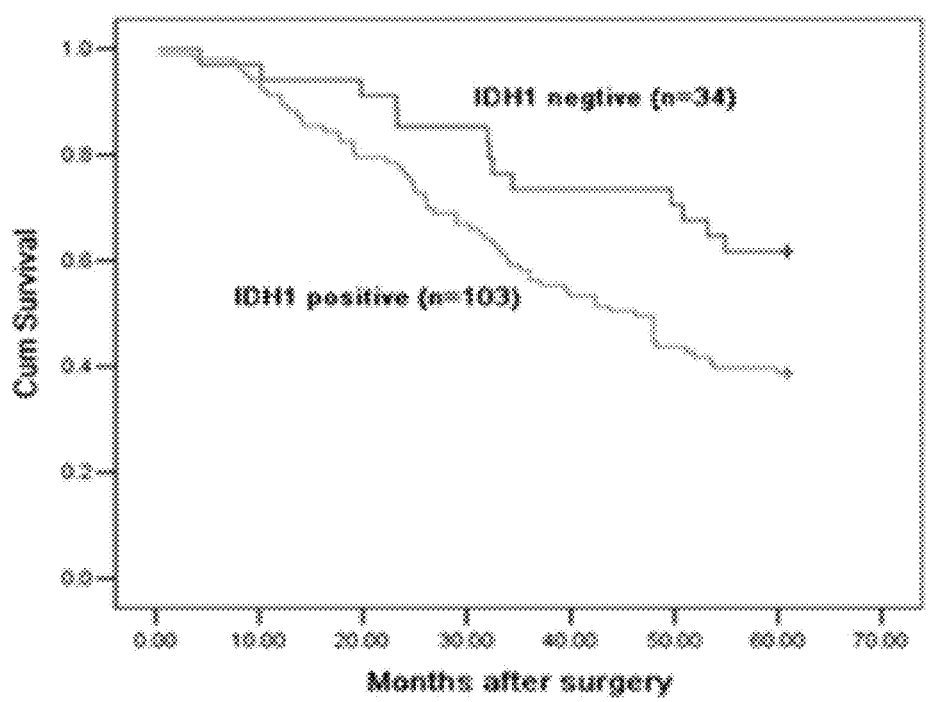
FIG. 3C

IDH1 positive is the independent prognostic parameter

| Variables (n=137) | | Univariate analysis | | Multivariate analysis | |
|---|---|---|---|---|---|
| | | Hazard ratio (95% CI) | p | Hazard ratio (95% CI) | p |
| T stage | T2-4/T1 | 9.524(1.330-68.667) | 0.025 | 8.130(1.116-59.824) | 0.039 |
| Lymph node metastasis | N1,N2/N0 | 2.778(1.686-4.565) | 0.000 | 2.123(1.256-3.584) | 0.005 |
| IDH1 | Positive/negtive | 1.992(1.096-3.623) | 0.024 | 1.973(1.054-3.693) | 0.034 |
| Differentiation | Poo/Middle,Well | 1.704(1.068-2.717) | 0.025 | 1.458(0.879-2.415) | 0.144 |
| Smoke | Smoke/Non-smoke | 1.745(1.103-2.761) | 0.017 | 1.559(0.913-2.660) | 0.104 |
| Gender | Female/Male | 1.645(1.022-2.646) | 0.040 | 1.149(0.660-2.000) | 0.624 |
| Pathology | AD/SCC | 1.460(0.930-2.291) | 0.100 | | |
| Age | ≥63/<63 | 1.536(0.969-2.433) | 0.068 | | |

FIG. 3D

| | AUC | Asymptotic Sig. | Sensitivity | Specificity | Youden Index |
|---|---|---|---|---|---|
| CYFRA21-1 | 0.762 | 0.000 | 74.0% | 67.6% | 0.42 |
| IDH1 | 0.749 | 0.000 | 76.5% | 63.8% | 0.40 |
| SCC-antigen | 0.740 | 0.000 | 55% | 85.7% | 0.41 |
| CEA | 0.582 | 0.018 | 43.0% | 76.2% | 0.19 |
| CA125 | 0.558 | 0.096 | 38.5% | 76.2% | 0.15 |

USE OF ISOCITRATE DEHYDROGENASE 1 AS A DIAGNOSTIC AND PROGNOSTIC BIOMARKER AND THERAPEUTIC TARGET FOR LUNG CANCERS

CROSS REFERENCE TO RELATED APPLICATIONS

The present application is a divisional application of U.S. patent application Ser. No. 14/428,334, entitled "USE OF ISOCITRATE DEHYDROGENASE 1 AS A DIAGNOSTIC AND PROGNOSTIC BIOMARKER AND THERAPEUTIC TARGET FOR LUNG CANCERS," filed on May 20, 2015. U.S. patent application Ser. No. 14/428,334 is a U.S. National Phase of International Patent Application Serial No. PCT/CN2012/081327, entitled "ISOCITRATE DEHYDROGENASE 1 AS A DIAGNOSTIC AND PROGNOSTIC BIOMARKER AND THERAPEUTIC TARGET FOR LUNG CANCERS," filed on Sep. 13, 2012. The entire contents of each of the above-referenced applications are hereby incorporated by reference for all purposes.

INCORPORATION BY REFERENCE OF ELECTRONICALLY SUBMITTED MATERIAL

Incorporated by reference in its entirety herein is a computer-readable nucleotide sequence listing submitted herewith and identified as follows: 3,201 bytes ASCII (Text) file named "Sequence_Listing_JEE15301PCTUSDIV," created Sep. 28, 2017.

FIELD OF THE INVENTION

The present invention generally relates to medical diagnostics and more specifically to the use of isocitrate dehydrogenase 1 (IDH1) as a diagnostic and prognostic biomarker and therapeutic target for lung cancers, particularly non-small cell lung cancer and to methods for diagnosing and determining the prognosis of lung cancers and treating lung cancers in a subject.

BACKGROUND OF THE INVENTION

Lung cancer is the leading cause of cancer-related death in the world. Approximately, 1.2 million people are diagnosed with lung cancer all over the world per year. Despite the great progresses in cancer research over the last decades, lung cancer has a very low 5-year survival rate of 16% as compared to 89% for breast cancer, 65% for colon cancer, and 100% for prostate cancer (1). While lung cancer comprises only about 15% of new cancer diagnoses, it causes over 30% of all cancer-related deaths. Lung cancer is divided into 2 major clinicopathological classes: small cell lung cancer (SCLC, about 15% of all lung cancer) and non-small cell lung cancer (NSCLC, about 85%). The latter includes three major histological subtypes: squamous cell carcinoma (SCC, 40% of NSCLC), adenocarcinoma (AD, 40% of NSCLC) and large cell carcinoma (10% of NSCLC) (2). NSCLC is commonly treated with surgery, while SCLC usually responds better to chemotherapy and radiotherapy. For NSCLC, curative surgery is efficacious only in those who are diagnosed sufficiently early. Unfortunately, more than 70% of the patients are diagnosed only at an advanced stage, which results in a lost opportunity for curative surgical resection, and poor prognosis. To improve the survival of patients with lung cancer, identifying reliable biomarkers for early diagnosis, prognosis prediction, and monitoring treatment response remain urgently needed.

Proteomic analysis, a powerful tool for global evaluation of protein expression, has been widely applied in cancer research. Quantitative protein expression profiling allows efficient identification of accurate and reproducible differential expression values for proteins in multiple biological samples. Comparison of protein expression profiles between tumors and normal tissues and among different tumors may lead to discovery of clinically useful tumor biomarkers, new therapeutic targets and elucidation of molecular mechanisms of cancers (3, 4). Several previous studies have focused on the application of comparative proteomics in screening differentially expressed proteins in cell line or clinical specimens of lung cancer (5-17). Approximately 300 proteins have been identified through these studies, including oncoproteins, signal transduction proteins, metabolic enzymes, and so on. However, few of them have been analyzed for their correlation with clinicopathological characteristics of lung cancer patients to investigate the value for clinical applications and their function in lung tumorigenesis. So far, none of these molecules identified is implemented in routine clinical use yet, and reliable biomarkers of lung cancer are urgently needed (18).

SUMMARY OF THE INVENTION

The main object of this invention is to provide a method for diagnosing the lung cancers, such as non-small lung cancer in a subject.

Another object of the inventive process is to provide a method for predicting the prognosis of the lung cancers, such as non-small cell lung cancer in subject.

Another object of this invention is to provide a method for the lung cancer therapy, such as non-small cell lung cancer in subject.

In one aspect, the present invention relates to a method for diagnosing the lung cancers such as non-small lung cancer, for example, squamous cell carcinoma (SCC) and adenocarcinoma (AD).

In one embodiment, the method for diagnosing the lung cancers comprises detecting the mRNA level of IDH1 in tumor tissues or cells, for example, by using PCR.

Specifically, the method uses a set of primers that allow specifically amplifying and obtaining an expected sequence of IDH1 to obtain a targeted fragment of IDH1 and makes a comparison between the amount of the target fragment of IDH1 and that of an internal reference such as human 18S rRNA as well as a comparison between the relative amount of the target fragment of IDH1 and that of a control. The method begins with total RNA isolation, whereby the cDNA is synthesized, and amplified by Taq DNA polymerase using the listed primer sequence in Table IV. Next, the expression of IDH1 gene is determined by analysis of relative amount of mRNA of IDH1 based on the amount of internal reference. The method also includes a step of administering a small molecule inhibitor specific to IDH1 to the subject if the comparison indicates a diagnosis of lung cancer. In one example, the small molecule inhibitor is an antibody specific to IDH1.

In another embodiment, the method for diagnosing lung cancers comprises a step of detecting protein levels of IDH1. Specifically, the invented method comprises use of an antibody against IDH1 to measure the protein level of IDH1, for example, by ELISA or by immunochemistry, and a comparison between the detected sample and the control based on the normalized data of control sample to determine the status of the sample detected. Detecting the protein levels of IDH1 comprises applying an antibody specific to IDH1 to the tumor tissue or cells or plasma sample of the subject, where presence of IDH1 creates an antibody-IDH1 complex, and applying a detection agent that detects the antibody-IDH1 complex. In some examples, the method may also include a step of administering a small molecule inhibitor specific to IDH1 to the subject if the comparison indicates a diagnosis of lung cancer. In one example, the small molecule inhibitor is an antibody specific to IDH1.

In another aspect, the present invention further provides a method for predicting the prognosis of the lung cancers, such as non-small cell lung cancer, for example, squamous cell carcinoma (SCC) and adenocarcinoma (AD) in a subject.

In one embodiment, the method for predicting the prognosis of the lung cancers comprises a step of detecting protein levels of IDH1 in a subject. Specifically, the invented method uses an antibody against IDH1 to measure the protein level of IDH1 in tumor tissue or cells or the plasma, for example, by ELISA or by immunochemistry.

In an embodiment, the method for predicting the prognosis of the lung cancer further comprises a comparison between the detected sample and the control based on the normalized data of control sample to determine the status of the sample detected.

In another aspect, the present invention further provides a method for predicting recurrence of lung cancer in a subject treated, such as non-small cell lung cancer, for example, squamous cell carcinoma (SCC) and adenocarcinoma (AD) in a subject.

In one embodiment, the method for predicting recurrence of lung cancers comprises detecting a protein level of IDH1 in the subject. Specifically, the invented method uses an antibody against IDH1 to measure the protein level of IDH1 in the plasma or tumor cells, for example, by ELISA or by immunohistochemistry.

In one embodiment, the method for predicting recurrence of lung cancers further comprises a step of comparison between the detected cells or plasma level of IDH1 and that of a control.

In an embodiment, generally, the subject is human, although as will be appreciated by those in the art, the subject may be an animal especially mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas).

In an embodiment, the lung cancer comprises a non-small lung cancer.

In one aspect, methods for detecting levels of IDH1 in plasma are well known to a person skilled in the art, for example, Enzyme-Linked Immunosorbent Assay (ELISA), immunoprecipitation (IP), immunohistochemistry, western blot, etc. ELISA is preferably used for the detection of IDH1.

In still an embodiment, the non-small lung cancer comprises squamous cell carcinoma (SCC) and adenocarcinoma (AD).

In an embodiment, the antibody used for the method may be commercially available.

In an embodiment, the PCR may be RT-PCR.

In another embodiment, the PCR may be a Real time PCR.

In another aspect, the present invention further provides method to suppress proliferation of lung tumor cells in a subject, which comprises knockdown or down-regulation of expression of IDH1.

In another aspect, the present invention further provides method to decrease growth of lung tumor cells in a subject, which comprises knockdown or down-regulation of expression of IDH1.

In another aspect, the present invention further provides method to improve survival of a subject with lung cancer, which comprises knockdown or down-regulation of expression of IDH1.

In another aspect, the present invention further provides method to suppress proliferation of lung tumor cells in a subject, which comprises administration of antibody specifically against IDH1 to the subject.

In another aspect, the present invention further provides method to decrease growth of lung tumor cells in a subject, which comprises administration of antibody specifically against IDH1 to the subject.

In another aspect, the present invention further provides method to improve survival of a subject with lung cancer, which comprises administration of antibody specifically against IDH1 to the subject.

Other aspects and embodiments of the present invention will become apparent to those of ordinary skill in the art upon review of the following detailed descriptions and examples of the invention in conjunction with the accompanying figures.

BRIEF DESCRIPTION OF THE DRAWINGS

In the figures, which illustrate embodiments of the invention by way of example only:

FIGS. 3A-3D are photos showing the results of immunohistochemical analysis of IDH1 expression in NSCLC tumors and paired normal lung tissues. FIGS. 3A and 3B show staining against IDH1 showed obviously increasing of IDH1 expression in tumors of both squamous cell carcinoma (FIG. 3A) and adenocarcinoma (FIG. 3B) compared with corresponding normal lung tissues. IDH1 proteins were strongly stained in the cytoplasm of tumor cells, but weakly or negatively expressed in normal respiratory bronchiolar cells and alveolar cells. FIG. 3C is a graph depicting Kaplan-Meier curves showing that IDH1 expression was related to decreased overall survival. Log-rank test was used. FIG. 3D is a table showing that multivariate analysis using the Cox proportional hazard model indicated that IDH1 positive staining as well as T stage and lymph node metastasis are independently prognostic factors.

FIG. 4A is a chart showing the distribution of IDH1 plasma level determined by ELISA in SCC patients, AD patients, healthy individuals and benign lung disease patients. Median values are shown by a horizontal line. Differences were significant between NSCLC patients and healthy individuals/benign lung disease patients (p<0.0001, respectively, Mann Whitney test), between SCC patients and healthy individuals/benign lung disease patients (p<0.0001, respectively), between AD patients and healthy individuals/benign lung disease patients (p=0.0002/p<0.0001). No significant difference between SCC patients and AD patients was observed (p=0.217). FIG. 4B is a chart showing the distribution of IDH1 in plasmas of patients with various TNM stages of NSCLC. No significant differences were observed among each stage (p=0.187, Kruskal-Wallis test). FIG. 4C is a chart showing ROC curves of IDH1, CYFRA21-1, SCC-antigen, CEA, and CA125 in discriminating NSCLC patients from controls (healthy individuals and benign lung disease patients). X axis, 1-specificity; Y axis, sensitivity. FIG. 4D is a table of calculations of the area under the curve (AUC) of each biomarker was listed along with the sensitivity and specificity of each biomarker at their optimal cutoff value, which was determined by maximizing the Youden index.

FIG. 5A is a western blot and chart of expression of IDH1 in 6 NSCLC cell lines and a normal bronchial epithelium cell line (upper). Beta-actin was used as internal control. The intensity values of IDH1 expression in various cell lines were normalized against those of controls and shown (lower). FIG. 5B shows an assessment of Anip973 cells stably transfected with two vectors expressing different shRNAs silencing IDH1 (sh-IDH1-1 and sh-IDH1-2) or negative control vector (sh-NC). Knockdown efficiencies of two independent shRNAs were assessed by Real-time PCR (upper) and Western blot (lower). FIG. 5C are charts showing proliferation of the cells stably transfected with sh-IDH1-1, sh-IDH1-2 and sh-NC were analyzed by CCK-8 assay. Data are expressed as mean±SD from 8 replicates in each group. In FIG. 5D, cells stably transfected with sh-IDH1-1 or sh-NC were injected subcutaneously in the right flank of athymic nude mice ($2\times10^6$ cells/mouse, 8 mice per group). Tumor volume was monitored at indicated times and tumor growth curve were plotted (upper). Data are expressed as mean±SD from 8 mice in each group. The mice were killed at day 28 and the xenograft tumors were weighed (middle) and shown (lower). Data shown are representative of three independent experiments.

DETAILED DESCRIPTION

Figure 1A:
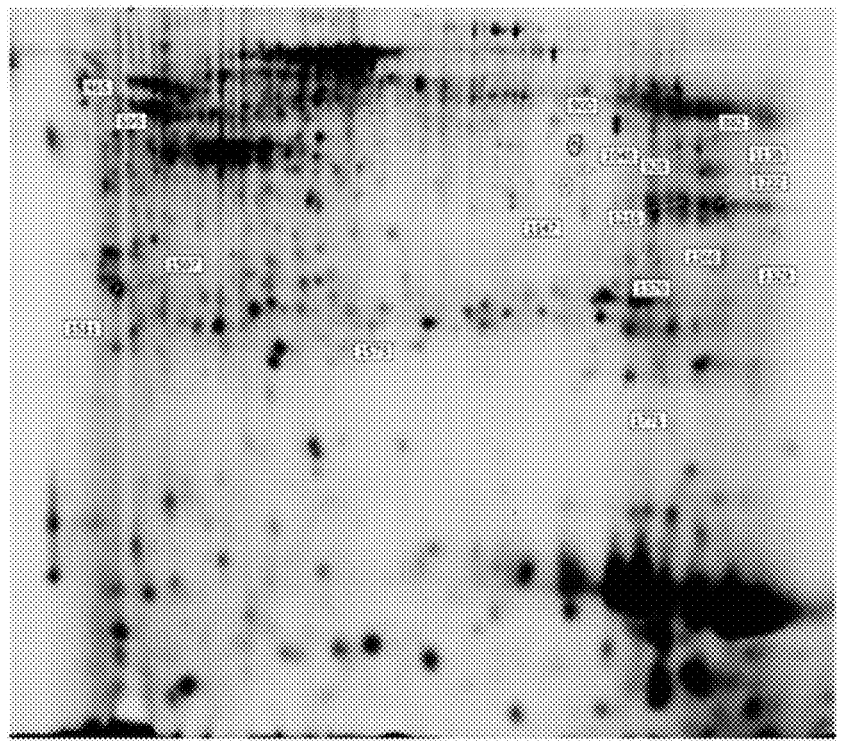
FIGS. 1A and 1B are representative two-dimensional gel images of the Cy2-labeled proteins that comprise the internal standard. The 36 identified protein spots are marked with master numbers and displayed. Protein spots up-regulated in tumors are identified in FIG. 1A. Protein spots down-regulated in tumors are identified in FIG. 1B.

The present invention is based on finding that the IDH1 is upregulated in lung tumors over paired normal tissues. IDH1, which catalyzes oxidative decarboxylation of isocitrate into α-ketoglutarate, is known as one of three enzymes responsible for production of NADPH in cytoplasm, and widely studied because of its cancer-related mutation in Arg-132. However, our findings show that IDH1 is upregulated in tumors of more than 70% of NSCLC, and increased IDH1 is correlated to a lower 5-year survival rate by immunohistochemistry staining.

In one aspect, the present invention provides a method for diagnosing the lung cancers, such as non-small lung cancer in a subject.

In one embodiment, the method for diagnosing the lung cancers comprises the steps of detecting the mRNA level of IDH1 using PCR.

Specifically, the present method comprises steps: a) providing RNA samples from a subject in need of such detection and a control; b) synthesizing cDNA from the RNA by reverse transcriptase; c) using a set of primers that allow specifically amplifying and obtaining expected sequence of IDH1 to obtain targeted fragment of IDH1; d) determining relative amount of target fragment of IDH1 based on the amount of internal reference such as human 18S rRNA; e) making a comparison between the relative amount of target fragment of IDH1 and that of control, thereby providing the information for diagnosis.

The primers used for amplification are designed for specifically amplifying and obtaining sequence of IDH1 the sequence and size of product of which is listed in Table IV.

The method begins with total RNA isolation from a sample of a subject. As used herein, the term "sample for extracting RNA" refers to any sample suitable for isolating the RNA. Sources of samples include whole blood, cells, or tissues (fresh or frozen) from a subject. In one embodiment, the sample is a blood sample, including, for example, whole blood or blood cells. A blood sample, suitable for use with the present invention, may be taken from any source known that includes blood cells, such as venous, arterial, peripheral, tissue.

The methods used to extract RNA may be any one conventionally known in the art. A commercially available kit may also be used for RNA isolation.

In one embodiment, PCR may be selected from RT-PCR and real-time PCR. RT-PCR is a routine method in the art and often used for semi-quantity expression level of RNA. The protocol for RT-PCR is commonly known to those skilled in the art. Depending on the primer used and the complexity of the fragment to be amplified, conditions for PCR can be determined by those skilled in the art based on common knowledge in the art.

After amplification of the expected fragment of IDH1, the expression of IDH1 mRNA is determined by analysis of the relative amount of mRNA of IDH1 relative to the amount of internal reference.

The internal references are internal standards for data normalization in relative measurement of mRNA in quantitative PCR or Real Time PCR. The genes used as internal references are formally called housekeeping genes which are thought to be constantly expressed in every cell or every tissue and are believed to be neither up nor down regulated. In one embodiment, the internal reference suitable for the present invention may be human 18S rRNA, β-actin or human GAPDH.

In another embodiment, the method for diagnosing lung cancers comprises detecting protein level of IDH1 in plasma or tumor tissue or cells of a subject. Specifically, the method described herein uses an antibody specifically against IDH1. The antibody against IDH1 may be from, for example, a commercially available kit.

The method for measuring the protein level of IDH1 in the plasma or tumor tissue or cells may use a routine method in the art, for example, immunohistochemistry, western blot, or ELISA. The method described herein may further comprise a comparison step, which is conducted between the detected sample and the control based on the normalized data of the control sample, to determine the status of the sample detected.

In another aspect, the present invention further provides a method for predicting the prognosis of lung cancers, such as non-small cell lung cancer, in subject.

The method for predicting the prognosis of lung cancers comprises the step of detecting levels of IDH1 in tumor tissue or cells or plasma in a subject. Specifically, the method described herein uses an antibody against IDH1 to measure the protein level of IDH1 in plasma, tumor tissue or cells. Preferably, the method for measuring the levels of IDH1 in tumor tissue, cells or plasma is immunochemistry, western blot, or enzyme-linked immunosorbent assay (ELISA), respectively.

The method for predicting the prognosis of the lung cancers further comprises comparison of the amount of detected sample with that of a control.

As commonly known in the art, bad prognosis usually means high rates of recurrence in treated patients, and high levels of plasma IDH1 often suggests a high possibility of recurrence in a subject. So, the method for detecting tumor tissue or cell or plasma levels of IDH1 described herein may be used to predict the recurrence of lung cancer in a subject who receives various treatments. In other words, tumor tissue or cell or plasma levels of IDH1 may indicate the possibility of recurrence of lung cancer after treatments, the method for detecting levels of IDH1 in tumor tissue or cell or plasma may be used to monitor the occurrence of recurrence of lung cancer after treatments.

In the present inventive method, preferably, the method for detecting levels of IDH1 in tumor tissue or cell or plasma in a subject may comprise steps of a) provide a plasma samples from a subject in need of such detection and a control; b) immobilizing the IDH1 in the sample; c) enabling the reaction between the IDH1 in the sample and antibody against IDH1 to form a reaction complex; d) detecting the reaction complex.

In one embodiment, the immobilization of IDH1 in the sample may be conducted by coating onto a solid support, for example, an ELISA plate or membrane.

In the present invention, there are many methods for detection of the reaction complex in the art, for example, using various antibody labels, such as horseradish peroxidase labeled antibody, fluorescence labeled and chemiluminesence detection and so on.

In one embodiment, the method for detecting plasma levels of IDH1 is preferably ELISA.

As used herein, the term "control" refers to any sample suitable for the present inventive method. The control includes, for example, the tissues that exclude cancer cells, the healthy or benign tissue from a subject having or without lung cancer or IDH-negative plasma sample. Preferably, for the methods for predicting the prognosis, the control may be selected from IDH-negative plasma sample.

In one embodiment, the lung cancer comprises non-small cell lung cancer, for example, squamous cell carcinoma (SCC) and adenocarcinoma (AD). In an embodiment, the subject is human.

In an embodiment, the antibody may be from a commercially available kit.

In another aspect, the present invention further provides method to suppress proliferation of lung tumor cells in a subject, which comprises knockdown or down-regulation of expression of IDH1. In an embodiment, the knockdown or down-regulation of IDH1 is performed by RNA interference. In an embodiment, the subject is human. In an embodiment, the lung cancer is a non-small lung cancer. In an embodiment, the non-small lung cancer is squamous cell carcinoma (SCC) or adenocarcinoma (AD).

In another aspect, the present invention further provides methods to decrease growth of lung tumor cells in a subject, comprising knockdown or down-regulation of expression of IDH1. In an embodiment, the knockdown or down-regulation of IDH1 is performed by RNA interference. In an embodiment, the subject is human. In an embodiment, the lung cancer is a non-small lung cancer. In an embodiment, the non-small lung cancer is squamous cell carcinoma (SCC) or adenocarcinoma (AD).

In another aspect, the present invention further provides method to improve survival of a subject with lung cancer, which comprises knockdown or down-regulation of expression of IDH1. In an embodiment, the knockdown or down-regulation of IDH1 is performed by RNA interference. In an embodiment, the subject is human. In an embodiment, the lung cancer is a non-small lung cancer. In an embodiment, the non-small lung cancer is squamous cell carcinoma (SCC) or adenocarcinoma (AD).

In another aspect, the present invention further provides methods to suppress proliferation of lung tumor cells in a subject, comprising administration of antibodies specifically against IDH1. In an embodiment, the subject includes humans. In an embodiment, the lung cancer is a non-small lung cancer. In an embodiment, the non-small lung cancer is squamous cell carcinoma (SCC) or adenocarcinoma (AD).

In another aspect, the present invention further provides a method of decreasing growth of lung tumor cells in a subject, comprising administration of antibodies specifically against IDH1 to the subject. In an embodiment, the subject comprises a human. In an embodiment, the lung cancer is a non-small lung cancer. In an embodiment, the non-small lung cancer is squamous cell carcinoma (SCC) or adenocarcinoma (AD).

In another aspect, the present invention further provides a method to improve survival of a subject with lung cancer, comprising administration of antibodies specifically against IDH1 to the subject. In an embodiment, the subject comprises a human. In an embodiment, the lung cancer is a non-small lung cancer. In an embodiment, the non-small lung cancer is squamous cell carcinoma (SCC) or adenocarcinoma (AD).

The present inventions are further illustrated by the following non-limiting examples.

Examples

1. Experimental Procedures
1) 2D-DIGE:
Samples

All tissue and blood specimens were collected from patients in the Cancer Institute and Hospital, Chinese Academy of Medical Sciences (CAMS) with informed consent and agreement. None of these patients received antineoplastic therapy prior to surgery. All tissue samples were taken by experienced surgeons and examined independently by two experienced pathologists. For 2D-DIGE, 12 pairs of fresh primary lung SCC tumors and their corresponding adjacent normal tissues were obtained during 2007-2008 (Table 1). The independent 15 pairs of lung SCC samples were collected for RT-PCR and western blot. Necrotic tissue was excluded, and normal lung tissues were confirmed to contain no tumor cells by histopathologic evaluation. The samples were snap frozen in liquid nitrogen immediately after resection, and stored at −80° C. until use. For immunohistochemistry analysis, 137 paraffin-embedded lung tumors and paired adjacent normal lung tissues were randomly obtained from patients between 1999-2001. For the ELISA study, preoperative peripheral blood samples were obtained from 200 NSCLC patients (median age at 60 with a range of 34 to 79 years) during 2009-2010 including 100 SCCs and 100 ADs. 55 specimens of healthy individuals (median age at 53 with a range of 41 to 64 years) were donated on a voluntary basis. In addition, 50 benign lung disease samples were obtained from patients (median age at 53 with a range of 21 to 79 years) pathologically diagnosed as one of the following diseases (frequency of diagnosis is given in parentheses): lung chronic inflammatory (16), pulmonary tuberculosis (7), hamartoma (22), sclerosing haemangioma (2), inflammatory myofibroblastic tumor (3). For all the specimens, clinicopathological information (age, gender, pathology, differentiation, smoking history, and TNM stage) was available. The study was approved by the medical ethics committee of Cancer Institute and Hospital, CAMS.

2D-DIGE:

~0.5 g of tissue was ground into powder in liquid nitrogen with a precooled mortar and pestle. Samples were then homogenized on ice in 1 ml of lysis buffer (7 M urea, 2 M thiourea, 4% CHAPS, 30 mM Tris-HCl, pH 8.5, protease inhibitor mixture) using a glass homogenizer. After sonication on ice for 10 s using an ultrasonic processor, the samples were centrifuged for 30 min (40,000 g) to remove particulate materials. Protein concentrations were determined in duplicate by the Bradford method (Bio-Rad) and confirmed by SDS-PAGE.

The pH of the protein was adjusted to 8.5 by 50 mM NaOH, and the concentration was adjusted to 5 mg/ml with lysis buffer. Equal amounts of proteins from the 12 pairs of samples were pooled together as the internal standard. Tumor and nontumor counterparts of each patient were randomly labeled with Cy3 or Cy5, whereas internal standards were labeled with Cy2 using 400 pmol of fluorochrome/50 μg of protein. Labeling was performed for 30 min on ice in the dark. Reactions were then quenched by the addition of 1 μl of lysine (10 mM) for 10 min on ice in the dark.

Fifty-microgram Cy3- and Cy5-labeled samples from each patient were combined before mixing with 50 μg of Cy2-labeled internal standard. Then an equal volume of 2×sample buffer (7 M urea, 2 M thiourea, 4% CHAPS, 1% Bio-Lyte, pH 3-10, 20 mg/ml DTT) was added to the sample, and the total volume was made up to 410 μl with rehydration buffer (7 M urea, 2 M thiourea, 4% CHAPS, 0.5% Bio-Lyte, 10 mg/ml DTT).

Samples were actively rehydrated into 24-cm pH 3-10 IPG strips (Bio-Rad) at 17° C. for 12 h using a Protean IEF cell (Bio-Rad). Isoelectric focusing was performed for a total of 80 kV-h (ramped to 250 V in 30 min, held at 1000 V for 1 h, ramped to 10,000 V in 5 h, and held at 10,000 V for 60 kV-h). The IPG strips were equilibrated in equilibration buffer (6 M urea, 2% SDS, 50 mM Tris-HCl, pH 8.8, 30% glycerol) supplemented with 0.5% DTT for 15 min at room temperature followed by 4.5% iodoacetamide in equilibration buffer for another 15-min incubation at room temperature.

IPG strips were placed on the top of 12% homogeneous polyacrylamide gels that had been precast with low fluorescence glass plates using an Ettan DALT twelve gel caster. The second dimension SDS-PAGE was carried out using the Protean Plus system (Bio-Rad). After 2DE, gels were scanned on the Typhoon 9410 scanner with Ettan DALT gel alignment guides using excitation/emission wavelengths specific for Cy2 (488/520 nm), Cy3 (532/580 nm), and Cy5 (633/670 nm). The intensity was adjusted to ensure that the maximum volume of each image was within 60,000-90,000.

Analysis of 2D-DIGE was done using DeCyder 6.5 software (GE Healthcare) according to the manufacturer's recommendations. Briefly the DeCyder biological variation analysis module was used to detect spots (the estimated number of spots was 2500) and simultaneously match all 36 protein spot maps from 12 gels. All matches were also confirmed manually. The paired t test with false discovery rate (FDR) correction was used for statistical analysis of the data. Protein spots that were differentially expressed in tumors and normal tissues (ratio$\leq$−2 or ratio$\geq$2, p$\leq$0.05) were selected. Only spots altered in the same direction with their average ratio in at least 5 of the 12 patients were chosen for identification.

In-Gel Digestion

Spot picking was carried out with preparative gels. Two-dimensional electrophoresis was performed as described under "2D DIGE and Imaging" except that the IPG strips were loaded with 1000 μg of protein, and gels were stained with Coomassie Brilliant Blue. Protein spots of interest were excised and destained with 25 mM ammonium bicarbonate, 50% ACN. Gels were then dried completely by centrifugal lyophilization. In-gel digestion was performed with 0.01 μg/μl trypsin (Promega) in 25 mM ammonium bicarbonate for 15 h at 37° C. The supernatants were collected, and the tryptic peptides were extracted from the gel sequentially with 5% TFA at 40° C. for 1 h and with 2.5% TFA, 50% ACN at 30° C. for 1 h. The extracts were pooled and dried completely by centrifugal lyophilization.

Protein Identification

Peptide mixtures were redissolved in 0.5% TFA, and 1 μl of peptide solution was mixed with 1 μl of matrix (4-hydroxy-α-cyanocinnamic acid in 30% ACN, 0.1% TFA) before spotting on the target plate. MALDI-TOF mass spectrometry and tandem TOF/TOF mass spectrometry were carried out on a 4800 Proteomics Analyzer (Applied Biosystems). Peptide mass maps were acquired in positive reflection mode, averaging 1500 laser shots per MALDI-TOF spectrum and 3000 shots per TOF/TOF spectrum (the resolution was 20,000). The 4800 calibration mixtures (Applied Biosystems) were used to calibrate the spectrum to a mass tolerance within 0.1 Da. Parent mass peaks with a mass range of 600-4000 Da and minimum signal to noise ratio of 15 were picked out for tandem TOF/TOF analysis. Combined mass and mass/mass spectra were used to interrogate human sequences in the IPI human database v3.23 (which contains 66,619 protein entries) using the MASCOT database search algorithms (version 2.1). Searches were performed to allow for carbamidomethylation, oxidation, and a maximum of one missed trypsin cleavage. Peptide tolerance and MS/MS tolerance were both 0.2 Da. All of the automatic data analysis and database searching were fulfilled by the GPS Explorer™ software (version 3.6, Applied Biosystems). Known contaminant ions (keratin) were excluded. The confident identification had a statistically significant (p$\leq$0.05) protein score (based on combined mass and mass/mass spectra). Redundancy of proteins that appeared in the database under different names and accession numbers was eliminated. The spots, in which more than one protein was identified, were excluded.

2) Semi-Quantitative RT-PCR

Total RNA was isolated from frozen tissues using the Trizol method (Invitrogen, Carlsbad, Calif., USA) following the manufacturer's instructions. The first strand cDNA was synthesized from 2 μg of total RNA using RevertAid first strand cDNA synthesis kit (Fermentas, Waltham, Mass., USA). For semi-quantitative PCR analysis, cDNA was amplified by Taq DNA polymerase (Takara, Kusatsu, Shiga Prefecture, Japan). Human 18S rRNA gene was used as an internal control. The primer sequences and the expected sizes of PCR products were listed Table IV. RT-PCR was performed with conditions as follows: denaturation at 94° C. for 2 min; then amplification for 28 cycles at 94° C. for 0.5 min, annealing at 60° C. for 0.5 min, and extension at 72° C. for 0.5 min; and then a terminal elongation step at 72° C. for 10 min and a final holding stage at 4° C.

3) Western Blot

Proteins from paired tumors and normal lung tissues or Anip973 cells were extracted and separated by SDS-PAGE and transferred to nitrocellulose membranes (Millipore, Billerica, Mass., USA). These blots were incubated for 1 h at room temperature in TBS-Tween 20 (TBST) containing 5% skim milk. Primary antibodies used were anti-IDH1 polyclonal antibody (diluted 1:1000, Abcam, Cambridge, Mass., USA), anti-SOD2 monoclonal antibody (diluted 1:1000, Epitomics, Cambridge, Mass., USA), anti-14-3-3 epsilon polyclonal antibody (diluted 1:2500, Abcam, Cambridge, Mass., USA), anti-RACK1 monoclonal antibody (diluted 1:2000, BD Biosciences), anti-PRDX2 monoclonal antibody (diluted 1:1000, Epitomics, Cambridge, Mass., USA) and anti-β-actin monoclonal antibody (diluted 1:5000, Protein-Tech, Tucson, Ariz., USA). The blots were labeled with peroxidase-conjugated secondary antibody to rabbit or mouse IgG (KPL (SeraCare, Inc., Milford, Mass., USA) and visualized by ECL reagents (Millipore, Billerica, Mass., USA).

4) Immunohistochemistry Staining

Tissue microarray (TMA) containing 137 paired NSCLC tumors and corresponding adjacent normal lung tissues was using to examine IDH1 expression. Routine immunohistochemical-SP staining was carried out according to the manufacturer's protocol with anti-IDH1 antibody (diluted 1:100, Abcam, Cambridge, Mass., USA). The microscopic analysis of the slides was independently performed by 2 experienced pathologists in a blind fashion without knowledge of the information of patients. The intensity of cell immunostaining was scored as 0, 1, 2, and 3, and the percentage of positive cells was assigned as following categories: 0 (0%-5%), 1 (6%-25%), 2 (26%-50%), 3 (51%-75%), or 4 (76%-100%). The final scores of the sections were recorded as − (negative), + (weakly positive), ++ (positive), and +++ (strongly positive); the scores were based on the intensity and the number of cells staining.

5) Plasma Biomarker Detection

Plasma samples were prepared by collecting blood in EDTA tubes. Samples were centrifuged at 3,000 rpm for 20 min immediately following collection, removed supernatants, and stored in aliquots at −80° C. until use. Plasma levels of IDH1 were measured by ELISA using a commercially available kit (Uscn Life Science, Wuhan, China) according to the manufacturer's recommendations. Plasma levels of CYFRA21-1, CEA and CA125 were measured by electrochemiluminescence immunoassay (ECLIA, Roche Diagnostics, Basel, Switzerland). Plasma levels of SCC-antigen were measured by chemiluminescent assays (CMIA, Abbott Laboratories, Chicago, Ill., USA).

Cell Culture

The 6 human NSCLC cell lines included Anip973 (lung AD), A549 (lung carcinoma), H2170 (lung SCC), NCI-H322 (bronchioalveolar carcinoma), H460 (lung large cell carcinoma) and H520 (lung SCC). All NSCLC cells and HBE cells (HPV transformed normal bronchial epithelium cell line) were grown in monolayer in appropriate medium supplemented with 10% FBS and maintained at 37° C. in humidified air with 5% CO2.

Plasmid Constructions and Cell Transfection

Knockdown of the IDH1 (GeneBank accession number NM_005896.2) in Anip973 cells was performed by stable transfection of a shRNA-expressing vector. The pGPU6/GFP/Neo-sh-IDH1-1 (sh-IDH1-1, target sequence SEQ ID NO:1 5'-TAACTTTGAAGAAGGTGGTGG-3') and pGPU6/GFP/Neo-sh-IDH1-2 (sh-IDH1-2, target sequence SEQ ID NO:2 5'-GGTATGAGCATAGGCTCATCG-3') vectors were constructed and identified by GenePharma Co. (Shanghai, China). The pGPU6/GFP/Neo-sh-NC (sh-NC) which targets a sequence not found in the human, mouse or rat genome databases (SEQ ID NO:3 5'-GTTCTC-CGAACGTGTCACGT-3') was used as negative control.

The sh-IDH1-1, sh-IDH1-2 and sh-NC were transfected into Anip973 cells respectively using Lipofectamine 2000 (Invitrogen, Carlsbad, Calif., USA) according to the manufacturer's instructions. G418 (Amresco Inc., Solon, Ohio, USA) at a concentration of 0.8 mg/ml was used to select transfected cells. After selection for 2 weeks, the pools were analyzed by Real-time PCR and Western blot to detect IDH1 expression level.

Real-Time Quantitative PCR

To determine the expression of IDH1 gene in Anip973 cells transfected with IDH1-RNAi vector or control vector, total RNA was isolated with Trizol method (Invitrogen, Carlsbad, Calif., USA). The first strand cDNA was synthesized from 1 μg of total RNA using reagents from Fermentas. Real-time PCR (Applied Biosystems 7300 Real Time PCR system, Foster City, Calif., USA) was performed using custom SYBR assays (Takara Bio, Kusasu, Shiga Prefecture, Japan) following the manufacturer's instructions. Human 18S rRNA gene was used as an internal control. The same primers were used for amplifying IDH1 and 18s RNA in Real-time PCR as used in RT-PCR described above. All PCR reactions, including no-template controls, were performed in triplicate.

CCK-8 Assay

In vitro proliferation of the transfected cells was measured using CCK-8 assay. Anip973 cells stably transfected with sh-IDH1-1, sh-IDH1-2 or sh-NC vector were plated at a density of 2,000 cells per well onto 96-well plates. For 7 days, cell viability was measured using CCK-8 (Dojindo Laboratories, Japan) and quantified by SoftMax® Pro 5 program (Molecular Devices) at every day.

In Vivo Tumorigenesis—Anip973 cells stably transfected with sh-IDH1-1 or sh-NC vector were suspended in PBS, then injected subcutaneously in the right flank of athymic nude mice ($2\times10^6$ cells/mouse, 8 mice per group). Tumor growth curve was plotted by means of tumor volumes monitored at indicated times. Tumor volume was calculated according to the following formula: length×(width)$^2$/2. The mice were killed at day 28 and the xenograft tumors were dissected and weighed.

Statistical Analysis—The differences between tumors and paired normal lung tissues were evaluated by Wilcoxon matched pairs test, while the differences between plasma sample groups were evaluated by the Mann-Whitney U test using GraphPad Prism version 5 for Windows. Survival curves were generated according to the Kaplan-Meier method using SPSS 13.0 software, and the statistical analysis was performed by log-rank test. Multivariate analysis was evaluated by Cox proportional hazard models. Statistical significance was defined as $p \leq 0.05$.

2. Results

Differentially Expressed Proteins in Lung SCC Tumors and Paired Normal Lung Tissues To screen differentially expressed proteins, tumors and their adjacent normal tissues from lung SCC patients were analyzed by 2D-DIGE. 12 paired samples labeled with Cy3 or Cy5 were run in twelve gels along with a pooled standard labeled with Cy2, and the images were analyzed by Decyder 6.5 software. Among 2173 matched protein spots, 72 were up-regulated (Ratiotumor/normal≥2, p≤0.05; paired t-test with FDR correction) and 112 were down-regulated (Ratiotumor/normal≤−2, p≤0.05) in tumors versus normal tissues.

Figure 1B:
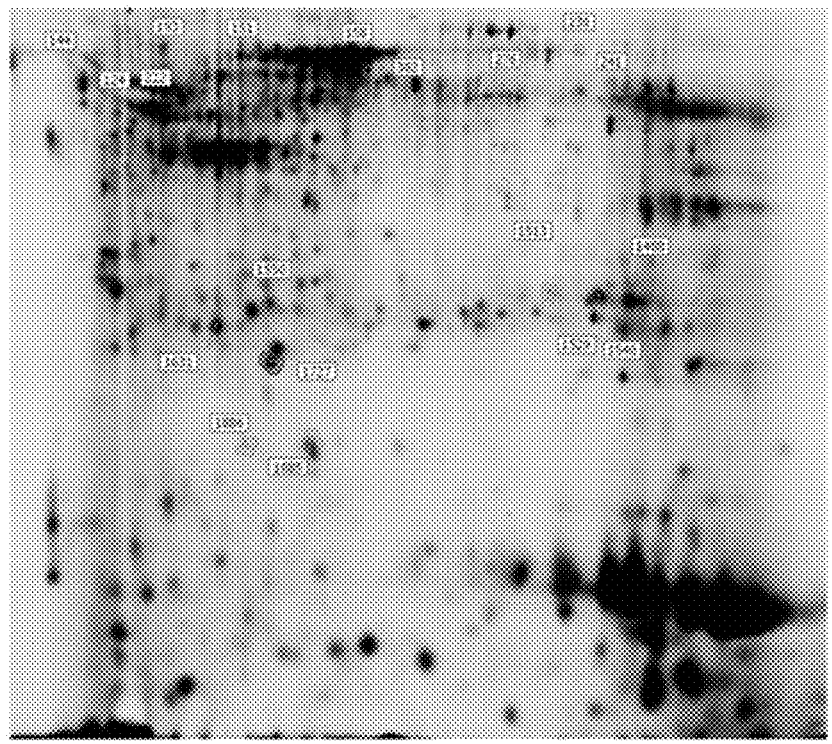

Identification of Differentially Expressed Proteins 53 differentially expressed protein spots showing sufficient intensity, clear separation from surrounding spots, and consistent spot shape and size were excised and subsequently in-gel digested by trypsin, then successfully analyzed by MALDI-TOF/TOF. The 9 spots identified as known contaminants (keratin 1, 2 and 10) and the 8 spots with multiple proteins identification were excluded from further analysis. Among those remaining 36 spots (17 up-regulated spots and 19 down-regulated spots shown in FIG. 1A and FIG. 1B respectively), 17 up-regulated and 11 down-regulated non-redundant proteins in tumor samples were identified.

Validating Expression of Certain Candidate Proteins by RT-PCR and Western Blot

We chose isocitrate dehydrogenase 1 (IDH1), superoxide dismutase 2 (SOD2), 14-3-3 epsilon, receptor of activated protein kinase C 1 (RACK1) and peroxiredoxin 2 (PRDX2) to be further validated by RT-PCR and Western blot, which were reported to be involved in some important pathways in tumor development and progression. Among them, IDH1, SOD2, 14-3-3 epsilon and RACK1 were up-regulated in tumors compared with corresponding normal lung tissues with an average ratio of 3.08, 2.16, 2.53 and 2.34 respectively by 2D-DIGE analysis. PRDX2 was identified as a tumor down-regulated protein with an average ratio of −2.11.

Figure 2A:
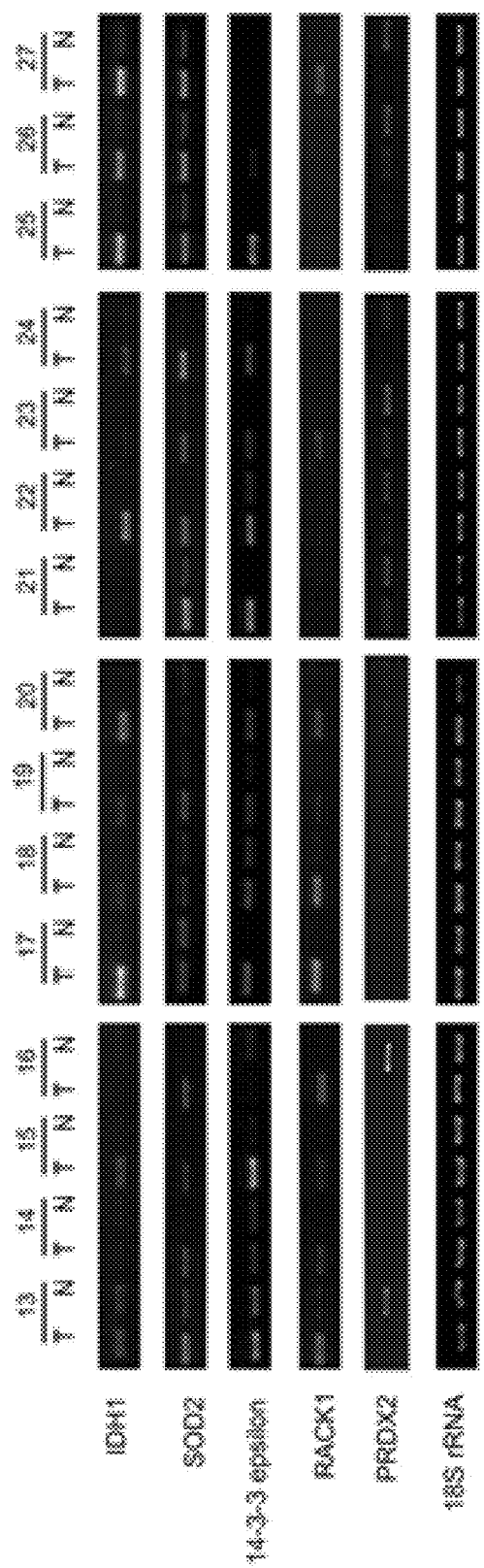
FIGS. 2A-2D depict validation of differential expression of IDH1, SOD2, 14-3-3 epsilon, RACK1 and PRDX2 in paired lung SCC tissues by semi-quantitative RT-PCR and western blot. Semi-quantitative RT-PCR (FIG. 2A) and western blot (FIG. 2C) were performed in independent 15 pairs of lung SCC tumors and corresponding normal tissues. 18sRNA and Beta-actin were used as internal controls. The agarose gel images (FIG. 2B) and western blot images (FIG. 2D) were quantified by densitometric scanning, and Wilcoxon matched pairs test was used after the intensity values were normalized against those of controls.
Figure 2B:
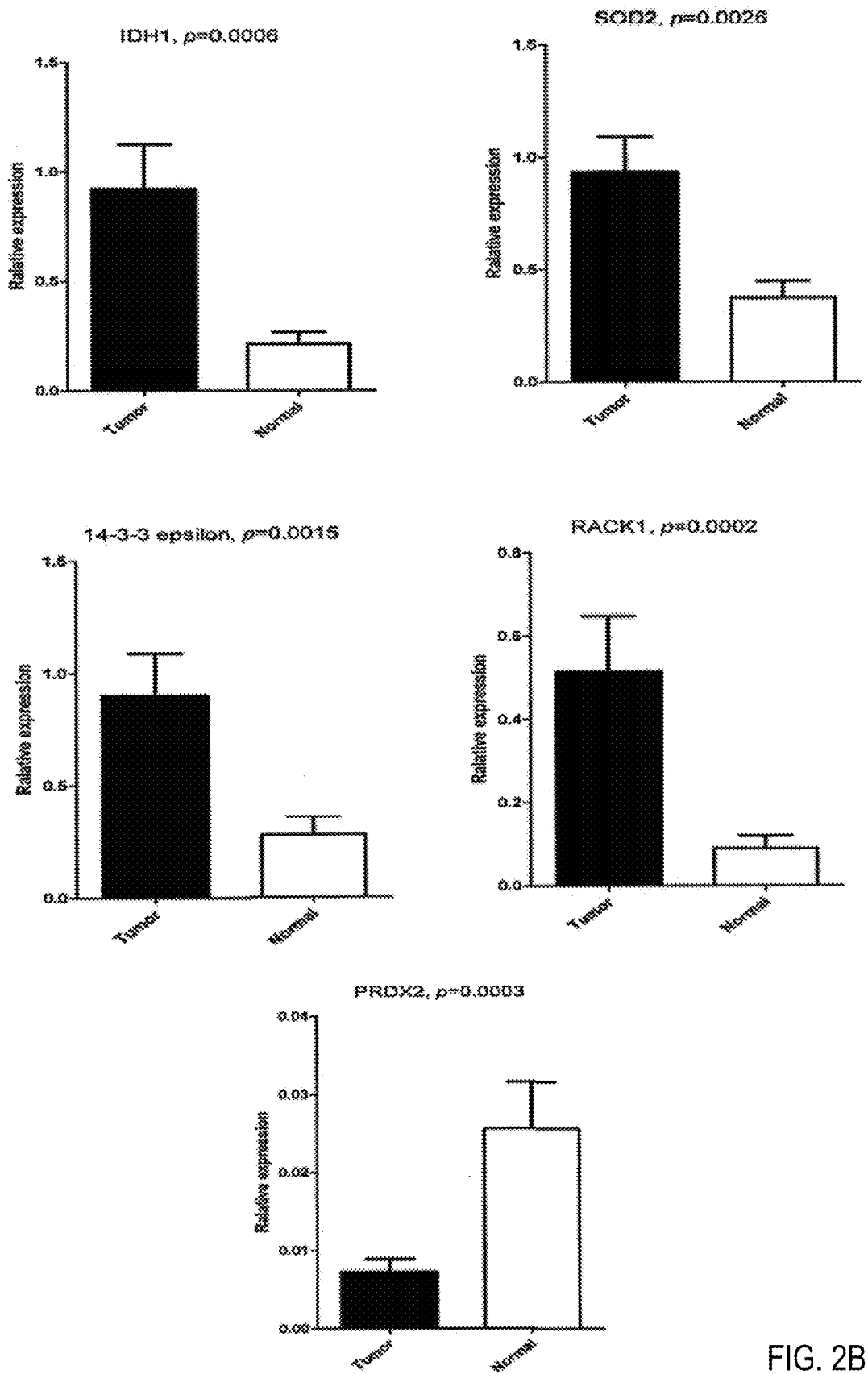
Figure 2C:
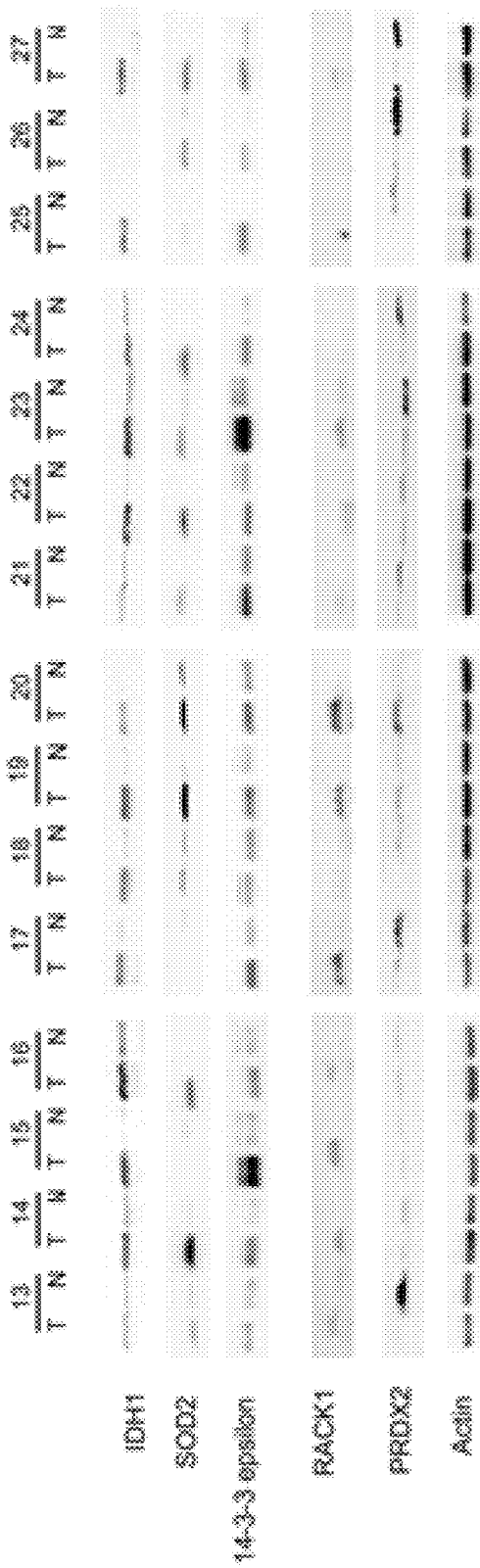
Figure 2D:
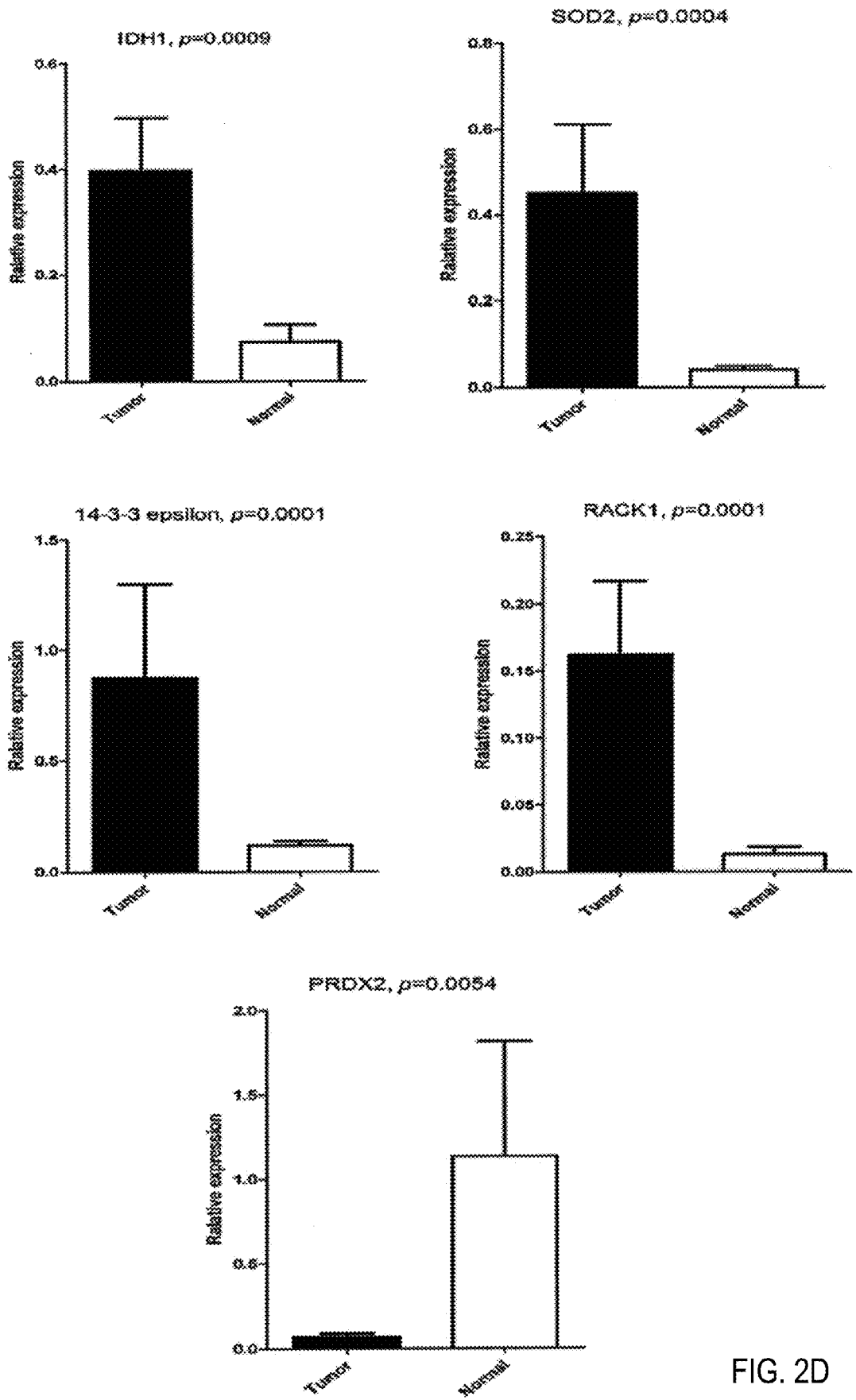

RT-PCR and Western blot were performed in independent 15 pairs of samples. RT-PCR showed that mRNA levels of IDH1, SOD2, 14-3-3 epsilon and RACK1 were significantly higher in tumors than those in paired normal lung tissues, whereas that of PRDX2 was lower in tumors (IDH1, 4.3 fold, $p=0.0006$; SOD2, 2.5 fold, $p=0.0026$; 14-3-3 epsilon, 3.3 fold, $p=0.0015$; RACK1, 5.7 fold, $p=0.0002$; PRDX2, −3.5 fold, $p=0.0003$; Wilcoxon matched pairs test) (FIGS. 2A and B). Western blot showed that the expression pattern of these five genes in protein level was identical with that in mRNA level. The abundance of IDH1, SOD2, 14-3-3 epsilon and RACK1 protein increased markedly in most of 15 tumors compared with their paired normal tissues, and PRDX2 proteins decreased in most tumors (IDH1, 5.3 fold, $p=0.0009$; SOD2, 11.1 fold, $p=0.0004$; 14-3-3 epsilon, 7.4 fold, $p=0.0001$; RACK1, 12.5 fold, $p=0.0001$; PRDX2, −16.7 fold, $p=0.0054$; Wilcoxon matched pairs test) (FIGS. 2C and D). These results were consistent with the observations in 2D-DIGE. The variation of the expression of these proteins may have been due to the heterogeneity of the samples.

Up-Regulation of IDH1 in Tumors by Immunohistochemistry

The expression of IDH1 was examined in formalin-fixed and paraffin-embedded tumor tissues and corresponding normal tissues from extended 73 SCC and 64 AD patients by immunohistochemistry using antibody against human IDH1. As shown in FIGS. 3A and B, the expression of IDH1 protein was located in the cytoplasm of tumor cells of SCC and AD. For SCC, the expression of IDH1 was significantly higher in tumor tissues with 72.6% positive staining, compared with paired normal lung tissues with only 8.2% positive staining (Chi-Square test, $p<0.001$) (FIG. 3A and Table II). Similarly to SCC, positive expression of IDH1 was detected in 78.1% of AD tumors, and only 7.9% of corresponding normal lung tissues (Chi-Square test, $p<0.001$) (FIG. 3B and Table II). No significant difference of IDH1 expression was found between tumors of SCC and AD (Chi-Square test, $p=0.849$). Totally, the IDH1 expression was significantly higher in this panel of 137 NSCLC tumors with 75.2% positive staining, compared with corresponding normal lung tissues, with only 8.1% positive staining (Chi-Square test, $p<0.001$) (Table II).

IDH1 is an Unfavorable Prognostic Factor for NSCLC

The correlation between expression of IDH1 and clinicopathological variables was evaluated by Chi-Square test. No significant correlation was observed between IDH1 expression and gender, age, smoking habit, family history, TNM stage, lymph node metastasis, tumor size (T stage), pathology and differentiation (Table III). However, the overall 5-year survival rate is significantly higher in IDH1-negative group than in IDH1-positive group (61.8% versus 38.8%, $p=0.020$). Kaplan-Meier survival analysis was further performed in 137 NSCLC patients. The survival curves showed that the patients with positive expression of IDH1 had a shorter survival than the patients with negative expression ($p=0.021$, Log-rank test) (FIG. 3C). To determine whether the prognostic value of IDH1 expression was independent of other risk factors associated with the clinical outcome of NSCLC, multivariate analysis was performed using the Cox proportional hazard model. Univariate Cox analysis showed that T stage, lymph node metastasis, IDH1 expression, differentiation, smoking habit and gender were significantly associated with survival of NSCLC patients. Subsequently, a multivariate Cox proportional hazard regression analysis using all these variables indicated that IDH1 expression was an independently unfavorable prognostic factor ($p=0.034$; risk ratio 1.973; 95% confidence interval [CI], 1.054-3.693) for NSCLC patients along with T stage ($p=0.039$; risk ratio 8.130; 95% confidence interval [CI], 1.116-58.824) and lymph node metastasis ($p=0.005$; risk ratio 2.123; 95% confidence interval [CI], 1.256-3.584) (FIG. 3D). These results suggested that IDH1 could be used as a histochemical biomarker for prognosis of NSCLC patients.

IDH1 is a Potential Plasma Biomarker for Diagnosis of NSCLC

Figure 4A:
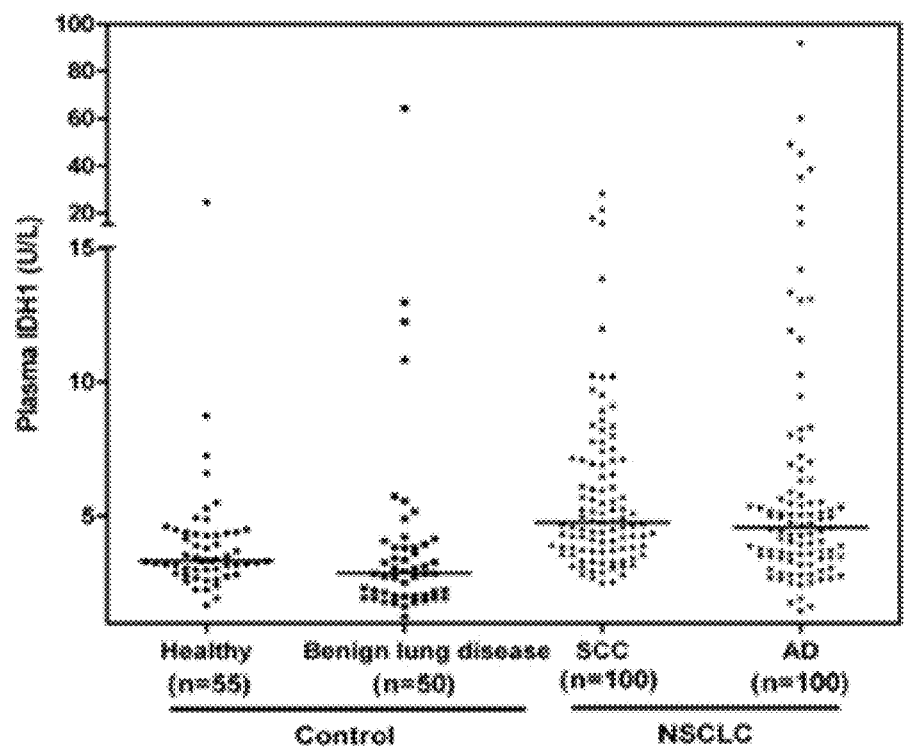
FIGS. 4A-4D show plasma levels of IDH1 and four conventional tumor biomarkers (CYFRA21-1, SCC-antigen, CEA, and CA125) in NSCLC patients, healthy individuals and benign lung disease patients.
Figure 4B:
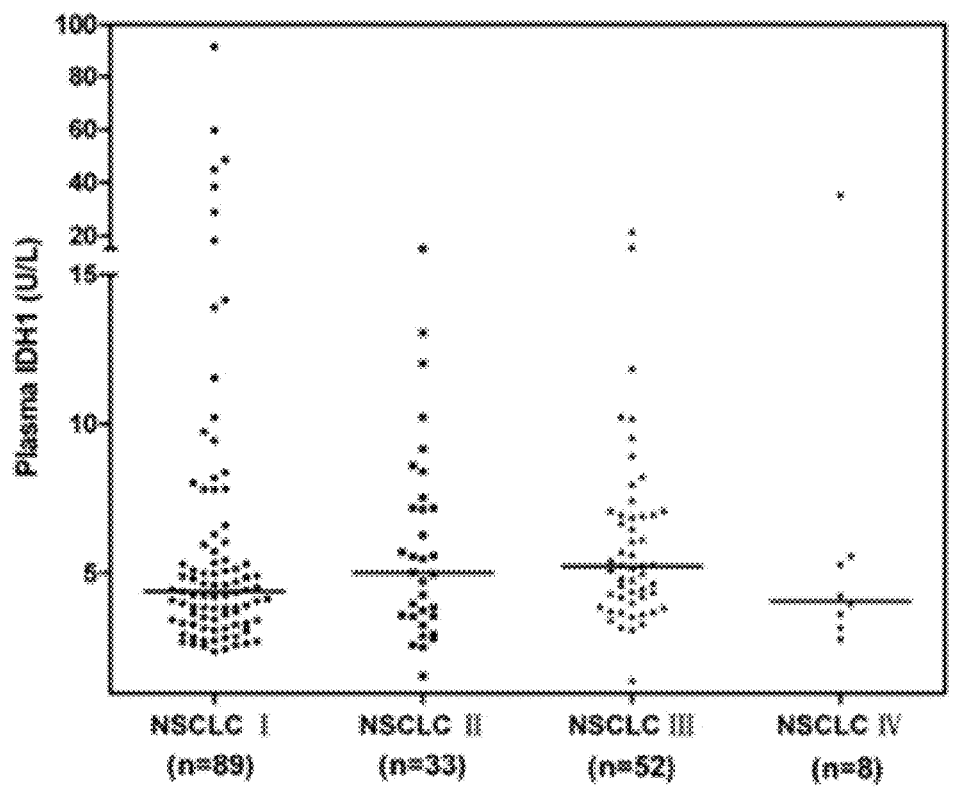

The plasma level of IDH1 and its potential value as a plasma biomarker for NSCLC was investigated. The plasma levels of IDH1 in 200 NSCLC patients (100 SCCs and 100 ADs), 55 healthy individuals and 50 benign lung disease patients were assessed by ELSIA. Plasma levels of IDH1 were significantly elevated in 200 NSCLC patients (Median=4.69 U/L) in comparison with 55 healthy individuals (Median=3.34 U/L; $p<0.0001$, Mann Whitney test) or 50 benign lung disease patients (Median=2.87 U/L; $p<0.0001$, Mann Whitney test) (FIG. 4A). According to histological types of NSCLC, the median plasma levels of IDH1 were 4.77 U/L in 100 SCC patients and 4.58 U/L in 100 AD patients; no significant difference between the two histological types was found ($p=0.2168$, Mann Whitney test). High levels of plasma IDH1 were detected even in patients with earlier-stage NSCLC, and no significant differences were observed among each stage ($p=0.1869$, Kruskal-Wallis test) (FIG. 4B).

Figures 4C, 4D:
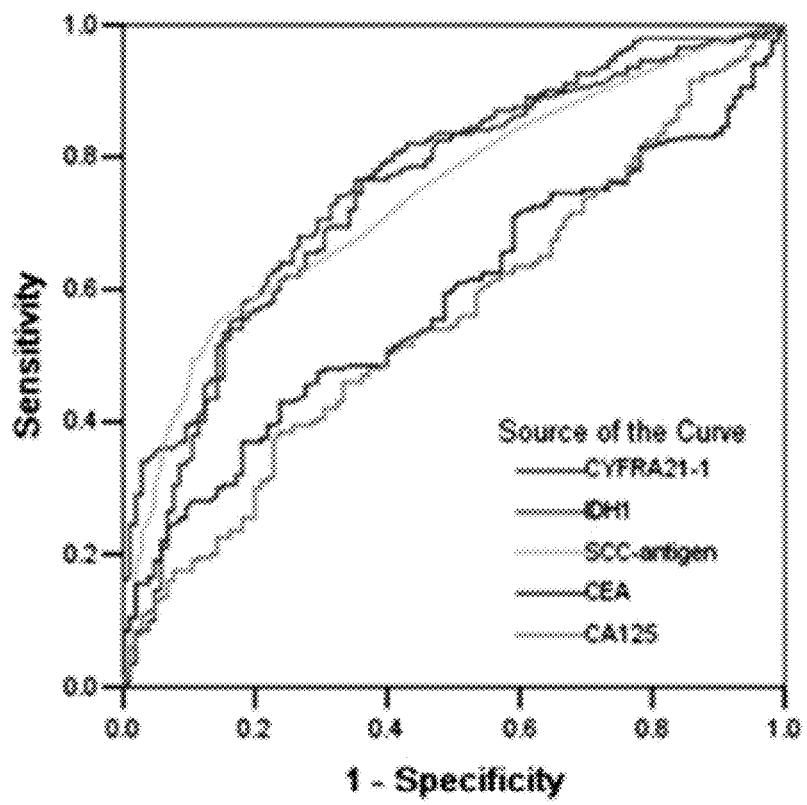

The receiver operating characteristic (ROC) curve of the plasma IDH1 levels of 200 NSCLC patients and 105 controls (55 healthy individuals and 50 benign lung disease patients) was shown in FIG. 4C. The area under the ROC curve (AUC) of IDH1 was 0.749, significantly higher than that of the null hypothesis (true area was 0.5; p=0.000) (FIG. 4D). To discriminate NSCLC patients from healthy individuals and benign lung disease patients, the optimal cutoff value of IDH1 level in plasma was 3.54 U/L in this study, at which the Youden index is maximized (0.40) with 76.5% sensitivity and 63.8% specificity. In addition to IDH1, four conventional NSCLC tumor markers (CYFRA21-1, SCC-antigen, CEA and CA125) were also measured, in the same set of plasma samples from cancer patients and control individuals. ROC analysis determined the optimal cutoff values to be 2.03 ng/mL for CYFRA21-1 (sensitivity 74.0%, specificity 67.6%, Youden index 0.42), 0.95 ng/mL for SCC-antigen (sensitivity 55.0%, specificity 85.7%, Youden index 0.41), 2.68 ng/mL for CEA (sensitivity 43.0%, specificity 76.2%, Youden index 0.19) and 14.7 U/mL for CA125 (sensitivity 38.5%, specificity 76.2%, Youden index 0.15). The AUC of IDH1 (0.749) was similar with CYFRA21-1 (0.762) and SCC-antigen (0.740), and larger than CEA (0.582) and CA125 (0.558) (FIG. 4D), suggesting that IDH1 has comparable diagnostic efficacy with CYFRA21-1 and SCC-antigen for NSCLC.

IDH1 Regulates NSCLC Cell Proliferation In Vitro and In Vivo

Figure 5A:
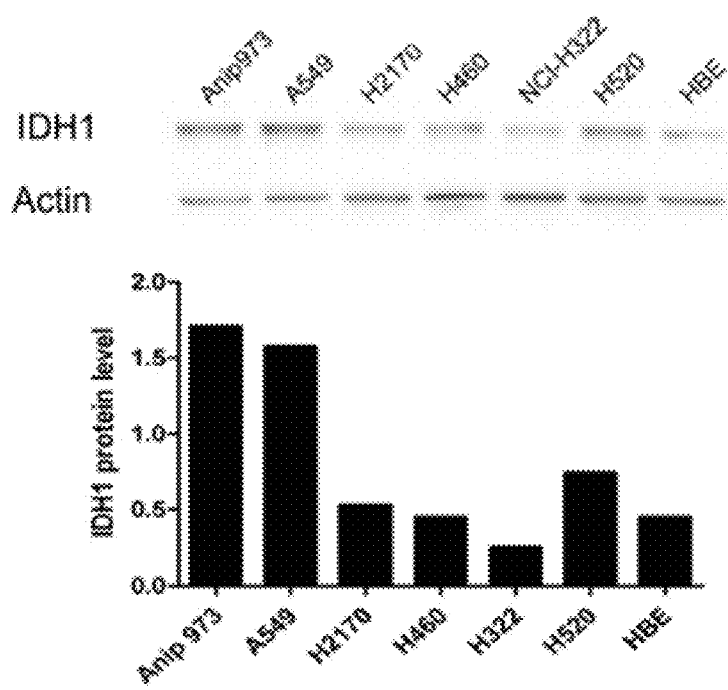
FIGS. 5A-5D depict tumor cell proliferation assessed by CCK-8 assays and tumor xenografts.
Figure 5B:
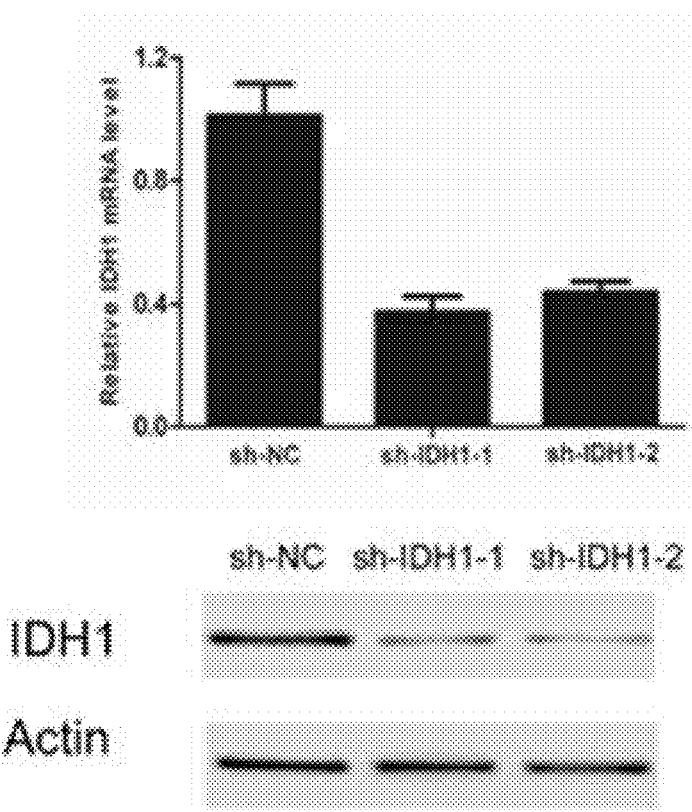
Figure 5C:
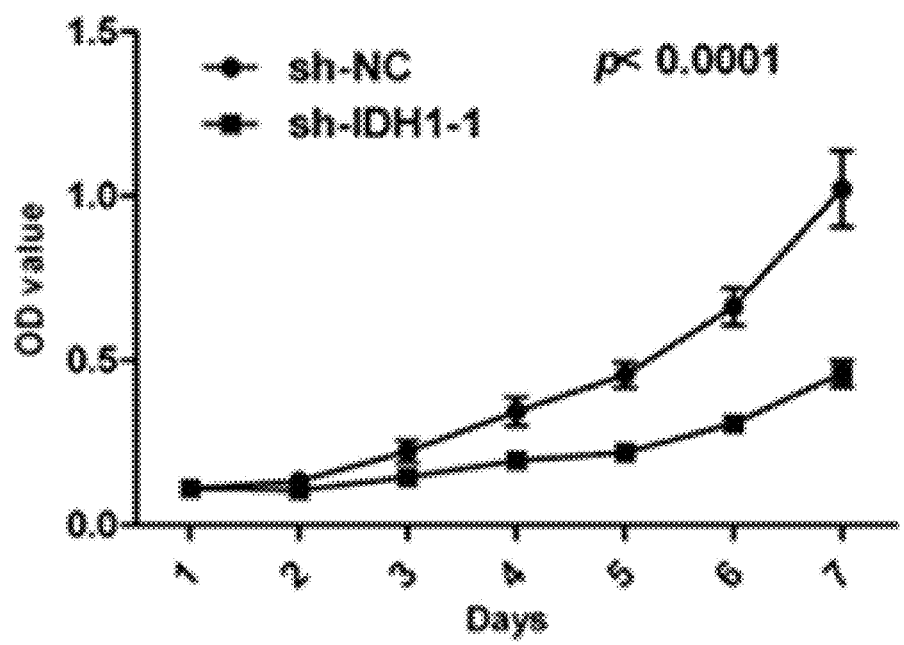
Figure 5C:
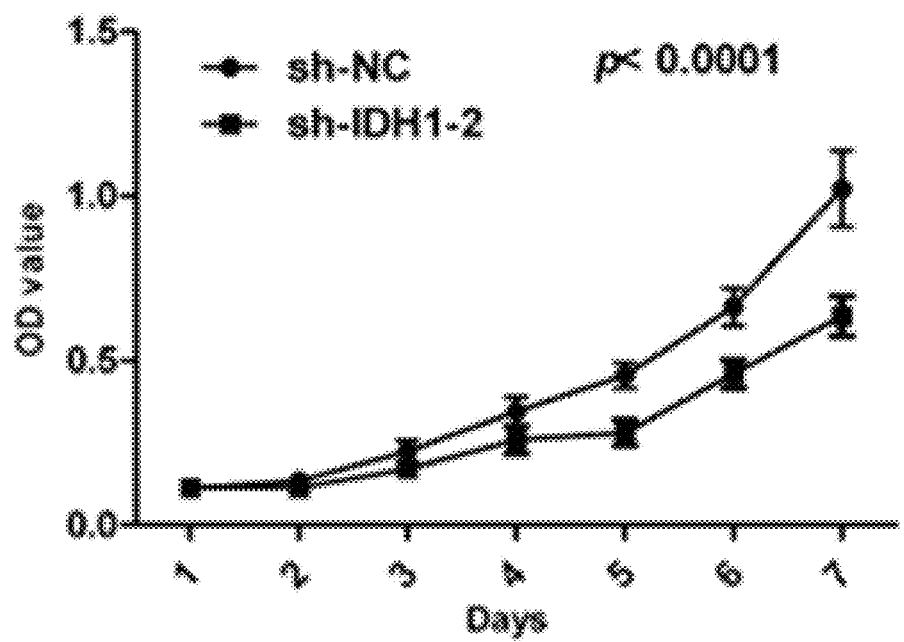
Figure 5D:
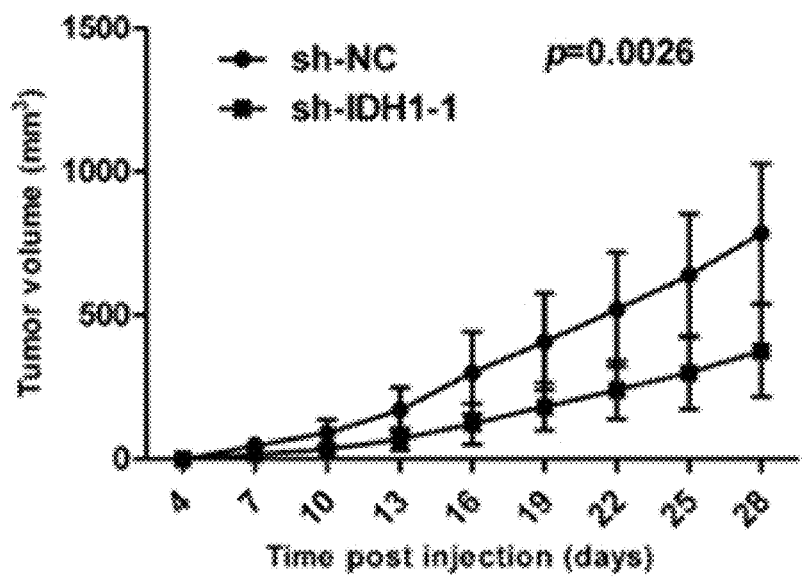
Figure 5D:
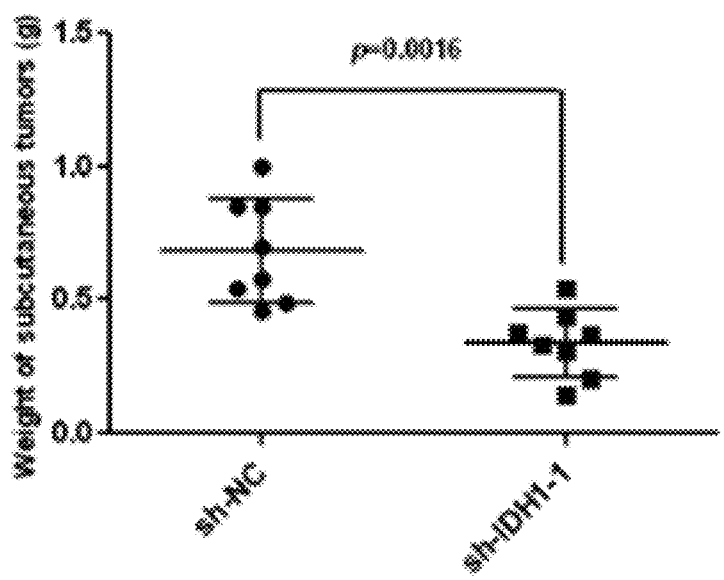
Figure 5D:
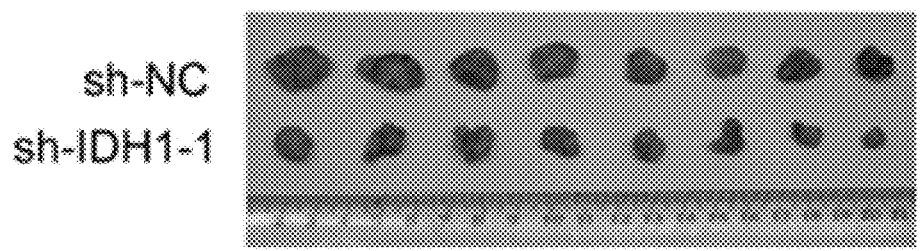

Expression of IDH1 in 6 NSCLC cell lines (Anip973, A549, H2170, H460, NCI-H322 and H520) was detected by Western blot, with a HPV transformed normal bronchial epithelium cell line (HBE) as control cell line. Higher IDH1 expression was observed in Anip973, A549 and H520 than in HBE cell line (FIG. 5A). To further investigate the effect of IDH1 on NSCLC tumor growth, Anip973 was stably transfected with shRNA-expressing vector to knock down the IDH1 expression. Real-time PCR and Western blot showed that IDH1 expression was markedly decreased in cells transfected with sh-IDH1-1 or sh-IDH1-2 vector compared to cells transfected with sh-NC vector (FIG. 5B). To investigate the effect of IDH1 knockdown on cell proliferation, growth of cells was assessed by CCK-8 assay. As shown in FIG. 5C, knockdown of IDH1 obviously decreased proliferation of Anip973 cells cultured in vitro. Furthermore, we evaluated the effect of IDH1 on tumor growth in vivo using xenograft model. Anip973 cells stably transfected with sh-IDH1-1 or sh-NC vector were implanted in nude mice subcutaneously, and tumor size was measured every 3 days. The mice were killed at day 28 and the tumors were dissected and weighed. As shown in FIG. 5D, the cells with IDH1 knockdown resulted in slower-growing xenografts as compared to cells with control vector. In 28 days, tumors from IDH1 knockdown cells were on average 50% smaller in weight than tumors from control cells (0.684 g versus 0.339 g, respectively; p=0.0016, t test) (FIG. 5D). The results indicated that the down-regulation of IDH1 expression decreased the growth of NSCLC tumor cells.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Tables

TABLE I

Clinical and pathologic information of 12 SCC patients

| Patients | TNM stage | Differentiation | Gender | Age |
|---|---|---|---|---|
| 1 | T2N0M0 | Middle | F | 63 |
| 2 | T2N0M0 | Middle | M | 66 |
| 3 | T2N0M0 | Low | M | 63 |
| 4 | T2N0M0 | Middle-low | M | 52 |
| 5 | T2N0M0 | Low | M | 57 |
| 6 | T2N0M0 | Low | M | 52 |
| 7 | T2N2M0 | Middle | M | 56 |
| 8 | T2N2M0 | Middle | M | 54 |
| 9 | T2N2M0 | Middle | M | 60 |
| 10 | T2N2M0 | Middle | M | 43 |
| 11 | T2N2M0 | Low | F | 53 |
| 12 | T2N2M0 | Low | M | 50 |

M, male;
F, female

TABLE II

Immunohistochemistry results for IDH1 in lung cancer patients
The scores of the tissue spots based on the intensity and the number of cells staining were recorded as − (negative), + (weakly positive), ++ (positive), and +++ (strongly positive). The proportions and numbers of samples with different immunohistochemistry staining results in tumors and normal tissues are listed in the Table. SCC, Squamous cancer; AD, Adenocarcinoma.

| | | Total cases | − | + | ++ | +++ | p value[a] |
|---|---|---|---|---|---|---|---|
| SCC | Tumor | 73 | 27.4% (20/73) | 27.4% (20/73) | 24.7% (18/73) | 20.5% (15/73) | <0.001 |
| | Normal | 73 | 91.8% (67/73) | 6.8% (5/73) | 1.4% (1/73) | 0 | |
| AD | Tumor | 64 | 21.9% (14/64) | 29.7% (19/64) | 23.4% (15/64) | 25.0% (16/64) | <0.001 |
| | Normal | 64 | 92.2% (59/64) | 6.3% (4/64) | 1.6% (1/64) | 0 | |

TABLE II-continued

Immunohistochemistry results for IDH1 in lung cancer patients
The scores of the tissue spots based on the intensity and the number of cells staining
were recorded as − (negative), + (weakly positive), ++ (positive), and +++ (strongly positive).
The proportions and numbers of samples with different immunohistochemistry staining results
in tumors and normal tissues are listed in the Table. SCC, Squamous cancer; AD, Adenocarcinoma.

|  |  | Total cases | − | + | ++ | +++ | p value[a] |
|---|---|---|---|---|---|---|---|
| SCC + AD | Tumor | 137 | 24.8% (34/137) | 28.5% (39/137) | 24.1% (33/137) | 22.6% (31/137) | <0.001 |
|  | Normal | 137 | 92.0% (126/137) | 6.6% (9/137) | 1.5% (2/137) | 0 |  |

[a]The p values of Chi-Square test

TABLE III

Correlation between IDH1 expression and clinicopathological factors of NSCLC patients

|  |  | IDH1 positive (Number of cases) | IDH1 negative (Number of cases) | P value[a] |
|---|---|---|---|---|
| Gender | Male | 70 | 27 | 0.203 |
|  | Female | 33 | 7 |  |
| Age | <63 | 48 | 15 | 0.801 |
|  | ≥63 | 55 | 19 |  |
| Smoking | Yes | 66 | 25 | 0.312 |
|  | No | 37 | 9 |  |
| Family history | Yes | 18 | 6 | 0.982 |
|  | No | 85 | 28 |  |
| TNM stage | I | 39 | 19 | 0.233 |
|  | II | 29 | 9 |  |
|  | III | 30 | 5 |  |
|  | IV | 5 | 1 |  |
| Lymph node metastasis | N0 | 40 | 20 | 0.107 |
|  | N1 | 29 | 9 |  |
|  | N2 | 32 | 4 |  |
|  | N3 | 2 | 1 |  |
| T stage | T1 | 10 | 1 | 0.417 |
|  | T2 | 85 | 32 |  |
|  | T3 | 7 | 1 |  |
|  | T4 | 1 | 0 |  |
| Pathology | SCC | 53 | 20 | 0.455 |
|  | AD | 50 | 14 |  |
| Differentiation | Well | 5 | 2 | 0.125 |
|  | Middle | 71 | 17 |  |
|  | Poor | 27 | 15 |  |
| 5-year survival | Yes | 40 | 21 | 0.020 |
|  | No | 63 | 13 |  |

[a]The p values of Chi-Square test

TABLE IV

Primers used in RT-PCR

| GENE |  |  |  | Primer (from 5' to 3') | Length |
|---|---|---|---|---|---|
| IDH1 | Sense | SEQ ID NO: | 4 | GTCGTCATGCTTATGGGGAT | 144 |
|  | Antisense | SEQ ID NO: | 5 | CAACACCACCACCTTCTTCA |  |
| SOD2 | Sense | SEQ ID NO: | 6 | TTGGCCAAGGGAGATGTTAC | 150 |
|  | Antisense | SEQ ID NO: | 7 | TTTGATGGCTTCCAGCAACT |  |
| 14-3-3 epsilon | Sense | SEQ ID NO: | 8 | GAGCGATACGACGAAATGGT | 289 |
|  | Antisense | SEQ ID NO: | 9 | TGTTAGCTGCTGGAATGAGG |  |
| RACK1 | Sense | SEQ ID NO: | 10 | AATACCCTGGGTGTGTGCAA | 144 |
|  | Antisense | SEQ ID NO: | 11 | AGCCAGGTTCCATACCTTGA |  |
| Peroxiredoxin2 | Sense | SEQ ID NO: | 12 | GGGCATTGCCTACAGGGGCC | 382 |
|  | Antisense | SEQ ID NO: | 13 | GGCCTAGCCCTCCAGGGTCC |  |
| 18S rRNA | Sense | SEQ ID NO: | 14 | CAGCCACCCGAGATTGAGCA | 253 |
|  | Antisense | SEQ ID NO: | 15 | TAGTAGCGACGGGCGGTGTG |  |

REFERENCES

1. Jemal, A., Siegel, R., Xu, J., and Ward, E. Cancer statistics, 2010. *CA: a cancer journal for clinicians* 60, 277-300.
2. Hoffman, P. C., Mauer, A. M., and Vokes, E. E. (2000) Lung cancer. *Lancet* 355, 479-485.
3. Simpson, R. J., Bernhard, O. K., Greening, D. W., and Moritz, R. L. (2008) Proteomics-driven cancer biomarker discovery: looking to the future. *Current opinion in chemical biology* 12, 72-77.
4. Cho, W. C., and Cheng, C. H. (2007) Oncoproteomics: current trends and future perspectives. *Expert review of proteomics* 4, 401-410.
5. Li, C., Xiao, Z., Chen, Z., Zhang, X., Li, J., Wu, X., Li, X., Yi, H., Li, M., Zhu, G., and Liang, S. (2006) Proteome analysis of human lung squamous carcinoma. *Proteomics* 6, 547-558.
6. Huang, L. J., Chen, S. X., Luo, W. J., Jiang, H. H., Zhang, P. F., and Yi, H. (2006) Proteomic analysis of secreted proteins of non-small cell lung cancer. *Chinese journal of cancer* 25, 1361-1367.
7. Maciel, C. M., Junqueira, M., Paschoal, M. E., Kawamura, M. T., Duarte, R. L., Carvalho Mda, G., and Domont, G. B. (2005) Differential proteomic serum pattern of low molecular weight proteins expressed by adenocarcinoma lung cancer patients. *Journal of experimental therapeutics & oncology* 5, 31-38.
8. Li, C., Chen, Z., Xiao, Z., Wu, X., Zhan, X., Zhang, X., Li, M., Li, J., Feng, X., Liang, S., Chen, P., and Xie, J. Y. (2003) Comparative proteomics analysis of human lung squamous carcinoma. *Biochemical and biophysical research communications* 309, 253-260.
9. Deng, B., Ye, N., Luo, G., Chen, X., and Wang, Y. (2005) Proteomics analysis of stage-specific proteins expressed in human squamous cell lung carcinoma tissues. *Cancer Biomark* 1, 279-286.
10. Li, C., Zhan, X., Li, M., Wu, X., Li, F., Li, J., Xiao, Z., Chen, Z., Feng, X., Chen, P., Xie, J., and Liang, S. (2003) Proteomic comparison of two-dimensional gel electrophoresis profiles from human lung squamous carcinoma and normal bronchial epithelial tissues. *Genomics, proteomics & bioinformatics/Beijing Genomics Institute* 1, 58-67.
11. Wu, X., Xiao, Z., Chen, Z., Li, C., Li, J., Feng, X., Yi, H., Liang, S., and Chen, P. (2004) Differential analysis of two-dimension gel electrophoresis profiles from the normal-metaplasia-dysplasia-carcinoma tissue of human bronchial epithelium. *Pathology international* 54, 765-773.
12. Chen, G., Gharib, T. G., Wang, H., Huang, C. C., Kuick, R., Thomas, D. G., Shedden, K. A., Misek, D. E., Taylor, J. M., Giordano, T. J., Kardia, S. L., Iannettoni, M. D., Yee, J., Hogg, P. J., Orringer, M. B., Hanash, S. M., and Beer, D. G. (2003) Protein profiles associated with survival in lung adenocarcinoma. *Proceedings of the National Academy of Sciences of the United States of America* 100, 13537-13542.
13. Chen, G., Gharib, T. G., Huang, C. C., Thomas, D. G., Shedden, K. A., Taylor, J. M., Kardia, S. L., Misek, D. E., Giordano, T. J., Iannettoni, M. D., Orringer, M. B., Hanash, S. M., and Beer, D. G. (2002) Proteomic analysis of lung adenocarcinoma: identification of a highly expressed set of proteins in tumors. *Clin Cancer Res* 8, 2298-2305.
14. Li, R., Wang, H., Bekele, B. N., Yin, Z., Caraway, N. P., Katz, R. L., Stass, S. A., and Jiang, F. (2006) Identification of putative oncogenes in lung adenocarcinoma by a comprehensive functional genomic approach. *Oncogene* 25, 2628-2635.
15. Seike, M., Kondo, T., Fujii, K., Yamada, T., Gemma, A., Kudoh, S., and Hirohashi, S. (2004) Proteomic signature of human cancer cells. *Proteomics* 4, 2776-2788.
16. Seike, M., Kondo, T., Fujii, K., Okano, T., Yamada, T., Matsuno, Y., Gemma, A., Kudoh, S., and Hirohashi, S. (2005) Proteomic signatures for histological types of lung cancer. *Proteomics* 5, 2939-2948.
17. Poschmann, G., Sitek, B., Sipos, B., Ulrich, A., Wiese, S., Stephan, C., Warscheid, B., Kloppel, G., Vander Borght, A., Ramaekers, F. C., Meyer, H. E., and Stuhler, K. (2009) Identification of proteomic differences between squamous cell carcinoma of the lung and bronchial epithelium. *Mol Cell Proteomics* 8, 1105-1116.
18. Buhrens, R. I., Amelung, J. T., Reymond, M. A., and Beshay, M. (2009) Protein expression in human non-small cell lung cancer: a systematic database. *Pathobiology* 76, 277-285.

The invention claimed is:

1. A method for diagnosing and treating non-small cell lung cancer in a subject comprising:
   (a) obtaining a first sample from the subject and a second sample from a control, each sample comprising nucleic acids or proteins;
   (b) determining an mRNA or protein level of isocitrate dehydrogenase 1 (IDH1) in the first sample of the subject using a PCR-based method or antibody-based method by comparison of mRNA or protein level between a relative mRNA or protein amount of IDH1 from the subject and a detected relative mRNA or protein amount of IDH1 from the control, wherein the relative mRNA or protein amount of IDH1 from the subject and the detected relative mRNA or protein amount of IDH1 from the control are each determined based on an amount of an internal reference;
   (c) diagnosing the subject as having non-small cell lung cancer if the comparison indicates that the subject has an expression of IDH1 greater than that of the control; and
   (d) administering an effective amount of an agent for down-regulation of expression of IDH1 to the diagnosed subject, wherein the agent is an RNA interfering agent and/or anti-IDH1 antibodies.

2. The method of claim 1, wherein the subject is human.

3. The method of claim 1, wherein the control is selected from tissues or cells that exclude cancer cells.

4. The method of claim 1, wherein the non-small lung cancer is squamous cell carcinoma (SCC) or adenocarcinoma (AD).

5. A method for predicting recurrence and treating lung cancers in a treated subject, comprising:
   (a) obtaining a first tumor cell or plasma sample from the treated subject and a second tumor cell or plasma sample from a control;
   (b) determining a protein level of isocitrate dehydrogenase 1 (IDH1) in the sample of the treated subject using an antibody-based method by comparison of the protein level between a relative protein amount of IDH1 from the treated subject and a detected relative protein amount of IDH1 from the control, wherein the relative protein amount of IDH1 from the treated subject and the detected relative protein amount of IDH1 from the control are each determined based on an amount of an internal reference;
   (c) predicting the treated subject as in a risk of recurrence of lung cancer if the comparison indicates that the treated subject has an expression of IDH1 greater than that of the control; and
   (d) administering an effective amount of an agent for down-regulation of expression of IDH1 to the treated subject predicted as in risk of recurrence of lung cancer, wherein the agent is an RNA interfering agent and/or anti-IDH1 antibodies.

6. The method of claim 5, wherein the treated subject is human.

7. The method of claim 5, wherein the control is IDH1 negative tissue, cell, or plasma.

8. The method of claim 5, wherein the lung cancer is non-small cell lung cancer.

9. The method of claim 8, wherein the non-small cell lung cancer is squamous cell carcinoma (SCC) or adenocarcinoma (AD).

10. The method of claim 1, wherein the PCR-based method comprises one or more of a RT-PCR and a real-time PCR.

11. The method of claim 1, wherein the antibody-based method comprises one or more of ELISA, immunoprecipitation, immunohistochemistry, and western-blot.

12. The method of claim 1, wherein primers specific for IDH1 and primers specific for the internal reference are used in the PCR-based method.

13. The method of claim 1, wherein the internal reference comprises one or more of 18S RNA, β-actin, and GAPDH.

14. The method of claim 5, wherein the antibody-based method comprises one or more of ELISA, immunoprecipitation, immunohistochemistry, and western-blot.

15. The method of claim 5, wherein the internal reference comprises one or more of β-actin and GAPDH.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: sh-IDH1-1

<400> SEQUENCE: 1
taactttgaa gaaggtggtg g                                            21

<210> SEQ ID NO 2
<211> LENGTH: 21
<212> TYPE: DNA
<213> ORGANISM: Artificial Sequence
<220> FEATURE:
<223> OTHER INFORMATION: sh-IDH1-2

<400> SEQUENCE: 2
```
ggtatgagca taggctcatc g                                         21

<210> SEQ ID NO 3
<211> LENGTH: 20
<212> TYPE: DNA
<213> ORGANISM: Artificial Sequence
<220> FEATURE:
<223> OTHER INFORMATION: sh-NC

<400> SEQUENCE: 3
gttctccgaa cgtgtcacgt                                           20

<210> SEQ ID NO 4
<211> LENGTH: 20
<212> TYPE: DNA
<213> ORGANISM: Artificial Sequence
<220> FEATURE:
<223> OTHER INFORMATION: Primer-IDH1-sense

<400> SEQUENCE: 4
gtcgtcatgc ttatggggat                                           20

<210> SEQ ID NO 5
<211> LENGTH: 20
<212> TYPE: DNA
<213> ORGANISM: Artificial Sequence
<220> FEATURE:
<223> OTHER INFORMATION: Primer-IDH1-antisense

<400> SEQUENCE: 5
caacaccacc accttcttca                                           20

<210> SEQ ID NO 6
<211> LENGTH: 20
<212> TYPE: DNA
<213> ORGANISM: Artificial Sequence
<220> FEATURE:
<223> OTHER INFORMATION: Primer-SOD2-sense

<400> SEQUENCE: 6
ttggccaagg gagatgttac                                           20

<210> SEQ ID NO 7
<211> LENGTH: 20
<212> TYPE: DNA
<213> ORGANISM: Artificial Sequence
<220> FEATURE:
<223> OTHER INFORMATION: Primer-SOD2-antisense

<400> SEQUENCE: 7
tttgatggct tccagcaact                                           20

<210> SEQ ID NO 8
<211> LENGTH: 20
<212> TYPE: DNA
<213> ORGANISM: Artificial Sequence
<220> FEATURE:
<223> OTHER INFORMATION: Primer-14-3-3 epsilon-sense

<400> SEQUENCE: 8
gagcgatacg acgaaatggt                                           20

<210> SEQ ID NO 9
<211> LENGTH: 20
<212> TYPE: DNA
<213> ORGANISM: Artificial Sequence

```
<220> FEATURE:
<223> OTHER INFORMATION: Primer-14-3-3 epsilon-antisense

<400> SEQUENCE: 9
tgttagctgc tggaatgagg                                               20

<210> SEQ ID NO 10
<211> LENGTH: 20
<212> TYPE: DNA
<213> ORGANISM: Artificial Sequence
<220> FEATURE:
<223> OTHER INFORMATION: Primer-RACK1-sense

<400> SEQUENCE: 10
aataccctgg gtgtgtgcaa                                               20

<210> SEQ ID NO 11
<211> LENGTH: 20
<212> TYPE: DNA
<213> ORGANISM: Artificial Sequence
<220> FEATURE:
<223> OTHER INFORMATION: Primer-RACK1-antisense

<400> SEQUENCE: 11
agccaggttc cataccttga                                               20

<210> SEQ ID NO 12
<211> LENGTH: 20
<212> TYPE: DNA
<213> ORGANISM: Artificial Sequence
<220> FEATURE:
<223> OTHER INFORMATION: Primer-Peroxiredoxin 2-sense

<400> SEQUENCE: 12
gggcattgcc tacaggggcc                                               20

<210> SEQ ID NO 13
<211> LENGTH: 20
<212> TYPE: DNA
<213> ORGANISM: Artificial Sequence
<220> FEATURE:
<223> OTHER INFORMATION: Primer-Peroxiredoxin 2-antisense

<400> SEQUENCE: 13
ggcctagccc tccagggtcc                                               20

<210> SEQ ID NO 14
<211> LENGTH: 20
<212> TYPE: DNA
<213> ORGANISM: Artificial Sequence
<220> FEATURE:
<223> OTHER INFORMATION: Primer-18S rRNA-sense

<400> SEQUENCE: 14
cagccacccg agattgagca                                               20

<210> SEQ ID NO 15
<211> LENGTH: 20
<212> TYPE: DNA
<213> ORGANISM: Artificial Sequence
<220> FEATURE:
<223> OTHER INFORMATION: Primer-18S rRNA-antisense

<400> SEQUENCE: 15
tagtagcgac gggcggtgtg                                               20
```